US008801768B2

(12) United States Patent
Karwa et al.

(10) Patent No.: US 8,801,768 B2
(45) Date of Patent: Aug. 12, 2014

(54) GRAFT SYSTEMS HAVING SEMI-PERMEABLE FILLING STRUCTURES AND METHODS FOR THEIR USE

(75) Inventors: Anupama Karwa, San Francisco, CA (US); Raj P. Ganpath, Sunnyvale, CA (US); Clark K. Colton, Newton, MA (US); K. T. Venkateswara Rao, San Jose, CA (US)

(73) Assignee: Endologix, Inc., Irvine, CA (US)

( * ) Notice: Subject to any disclaimer, the term of this patent is extended or adjusted under 35 U.S.C. 154(b) by 114 days.

(21) Appl. No.: 13/355,705

(22) Filed: Jan. 23, 2012

(65) Prior Publication Data
US 2012/0203264 A1 Aug. 9, 2012

Related U.S. Application Data

(60) Provisional application No. 61/434,954, filed on Jan. 21, 2011.

(51) Int. Cl.
*A61F 2/06* (2013.01)
(52) U.S. Cl.
USPC .......................................................... 623/1.11
(58) Field of Classification Search
USPC ................... 606/108, 200, 153; 424/422–424
See application file for complete search history.

(56) References Cited

U.S. PATENT DOCUMENTS

| 3,760,806 | A | * | 9/1973 | Leeper | 604/892.1 |
| 3,797,485 | A | * | 3/1974 | Urquhart | 604/288.04 |
| 4,157,085 | A | * | 6/1979 | Austad | 128/898 |
| 4,327,725 | A | * | 5/1982 | Cortese et al. | 424/427 |
| 4,565,738 | A | | 1/1986 | Purdy | |
| 4,638,803 | A | | 1/1987 | Rand | |

(Continued)

FOREIGN PATENT DOCUMENTS

| DE | 4010975 A1 | 10/1991 |
| EP | 95302708.3 | 11/1995 |

(Continued)

OTHER PUBLICATIONS

Patrick W. Serruys and Michael JB Kutryk; Handbook of Coronary Stents, Second Edition; 1998; pp. 45, 55, 78, 103, 112, 132, 158, 174, 185, 190, 207, 215, 230, 239; Martin Dunitz; UK.

(Continued)

*Primary Examiner* — Darwin Erezo
*Assistant Examiner* — Amy Shipley
(74) *Attorney, Agent, or Firm* — Kilpatrick Townsend & Stockton LLP; Kenneth R. Shurtz, Esq.

(57) ABSTRACT

Aneurysms are treated by filling at least one double-walled filling structure with a filling medium within the aneurysm, such as filling structures having a membrane that allows water molecules to permeate across the membrane in response to a water potential differential across the membrane. The transport of fluid across the membrane allows the bag to expand or shrink to accommodate changes in the size or shape of the aneurysm, thereby maintaining a seal between the filling structure against the vessel wall and maintaining apposition of the filling structure against the inside surface of the aneurysm. Transport of water molecules into or out of the filling structure is controlled by adjusting for the osmolarity of the filling fluid medium. The filling structures may be delivered over balloon deployment mechanisms in order to shape occlude the aneurysm and open a tubular lumen for flow of blood through the filling structure.

21 Claims, 26 Drawing Sheets

(56) References Cited

U.S. PATENT DOCUMENTS

| | | | |
|---|---|---|---|
| 4,641,653 A | 2/1987 | Rockey | |
| 4,686,776 A * | 8/1987 | Matsubara | 34/95 |
| 4,704,126 A | 11/1987 | Baswell | |
| 4,710,192 A | 12/1987 | Liotta | |
| 4,728,328 A | 3/1988 | Hughes et al. | |
| 4,731,073 A | 3/1988 | Robinson | |
| 4,733,665 A | 3/1988 | Palmaz | |
| 4,743,258 A | 5/1988 | Ikada | |
| 4,763,654 A | 8/1988 | Jang | |
| 4,856,516 A | 8/1989 | Hillstead | |
| 4,858,264 A | 8/1989 | Reinhart | |
| 4,892,544 A | 1/1990 | Frisch | |
| 4,936,057 A | 6/1990 | Rhoades | |
| 4,976,692 A | 12/1990 | Atad | |
| 5,002,532 A | 3/1991 | Gaiser | |
| 5,074,845 A | 12/1991 | Miraki | |
| 5,082,723 A * | 1/1992 | Gross et al. | 442/118 |
| 5,104,404 A | 4/1992 | Wolff | |
| 5,108,417 A | 4/1992 | Sawyer | |
| 5,122,154 A | 6/1992 | Rhodes | |
| 5,133,732 A | 7/1992 | Wiktor | |
| 5,139,480 A | 8/1992 | Hickle | |
| 5,156,620 A | 10/1992 | Pigott | |
| 5,195,984 A | 3/1993 | Schatz | |
| 5,199,226 A | 4/1993 | Rose | |
| 5,217,484 A | 6/1993 | Marks | |
| 5,222,970 A | 6/1993 | Reeves | |
| 5,234,437 A | 8/1993 | Sepetka | |
| 5,242,399 A | 9/1993 | Lau | |
| 5,250,071 A | 10/1993 | Palermo | |
| 5,261,916 A | 11/1993 | Engelson | |
| 5,263,964 A | 11/1993 | Purdy | |
| 5,292,331 A | 3/1994 | Houki et al. | |
| 5,314,444 A | 5/1994 | Gianturco | |
| 5,316,023 A | 5/1994 | Palmaz et al. | |
| 5,330,528 A | 7/1994 | Lazim | |
| 5,334,217 A | 8/1994 | Das | |
| 5,350,397 A | 9/1994 | Palermo | |
| 5,352,199 A | 10/1994 | Tower | |
| 5,375,612 A | 12/1994 | Cottenceau | |
| 5,383,892 A | 1/1995 | Cardon | |
| 5,421,955 A | 6/1995 | Lau | |
| 5,423,849 A | 6/1995 | Engelson | |
| 5,425,739 A | 6/1995 | Jessen | |
| 5,425,744 A | 6/1995 | Fagan | |
| 5,441,510 A | 8/1995 | Simpson | |
| 5,441,515 A | 8/1995 | Khosravi | |
| 5,443,477 A | 8/1995 | Marin | |
| 5,443,496 A | 8/1995 | Schwartz | |
| 5,449,373 A | 9/1995 | Pinchasik | |
| 5,485,667 A | 1/1996 | Kleshinski | |
| 5,494,029 A | 2/1996 | Lane | |
| 5,496,277 A | 3/1996 | Termin | |
| 5,496,368 A * | 3/1996 | Wiese | 623/8 |
| 5,499,994 A * | 3/1996 | Tihon et al. | 606/192 |
| 5,507,767 A | 4/1996 | Maeda | |
| 5,507,769 A | 4/1996 | Marin et al. | |
| 5,507,771 A | 4/1996 | Gianturco | |
| 5,514,115 A | 5/1996 | Frantzen | |
| 5,514,154 A | 5/1996 | Lau | |
| 5,522,882 A | 6/1996 | Gaterud | |
| 5,530,528 A | 6/1996 | Houki et al. | |
| 5,531,741 A | 7/1996 | Barbacci | |
| 5,534,024 A | 7/1996 | Rogers et al. | |
| 5,545,210 A | 8/1996 | Hess | |
| 5,547,378 A * | 8/1996 | Linkow | 433/173 |
| 5,549,662 A | 8/1996 | Fordenbacher | |
| 5,549,663 A | 8/1996 | Cottone, Jr. | |
| 5,554,181 A | 9/1996 | Das | |
| 5,562,641 A | 10/1996 | Flomenblit | |
| 5,562,698 A | 10/1996 | Parker | |
| 5,562,728 A | 10/1996 | Lazarus | |
| 5,569,295 A | 10/1996 | Lam | |
| 5,578,074 A | 11/1996 | Mirigian | |
| 5,578,149 A | 11/1996 | De Scheerder | |
| 5,591,195 A | 1/1997 | Taheri | |
| 5,591,223 A | 1/1997 | Lock | |
| 5,591,226 A | 1/1997 | Trerotola | |
| 5,591,228 A | 1/1997 | Edoga | |
| 5,591,230 A | 1/1997 | Horn | |
| 5,593,417 A | 1/1997 | Rhodes | |
| 5,601,600 A | 2/1997 | Ton | |
| 5,603,721 A | 2/1997 | Lau | |
| 5,605,530 A | 2/1997 | Fischell | |
| 5,607,442 A | 3/1997 | Fischell | |
| 5,607,445 A | 3/1997 | Summers | |
| 5,607,468 A | 3/1997 | Rogers | |
| 5,609,605 A | 3/1997 | Marshall | |
| 5,617,878 A | 4/1997 | Taheri | |
| 5,618,299 A | 4/1997 | Khosravi | |
| 5,624,411 A | 4/1997 | Tuch | |
| 5,630,840 A | 5/1997 | Mayer | |
| 5,632,760 A | 5/1997 | Sheiban | |
| 5,632,762 A | 5/1997 | Myler | |
| 5,632,763 A | 5/1997 | Glastra | |
| 5,632,771 A | 5/1997 | Boatman | |
| D380,266 S | 6/1997 | Boatman | |
| 5,634,941 A | 6/1997 | Winston | |
| 5,636,641 A | 6/1997 | Fariabi | |
| D380,831 S | 7/1997 | Kavteladze | |
| 5,662,614 A | 9/1997 | Edoga | |
| 5,665,117 A | 9/1997 | Rhodes | |
| 5,674,241 A | 10/1997 | Bley | |
| 5,676,697 A | 10/1997 | McDonald | |
| 5,683,449 A | 11/1997 | Marcade | |
| 5,690,643 A | 11/1997 | WiJay | |
| 5,693,038 A | 12/1997 | Suzuki et al. | |
| 5,693,067 A | 12/1997 | Purdy | |
| 5,693,088 A | 12/1997 | Lazarus | |
| 5,697,971 A | 12/1997 | Fischell | |
| 5,709,707 A | 1/1998 | Lock | |
| 5,718,713 A | 2/1998 | Frantzen | |
| 5,723,004 A | 3/1998 | Dereume | |
| 5,725,568 A | 3/1998 | Hastings | |
| 5,725,572 A | 3/1998 | Lam | |
| 5,728,068 A | 3/1998 | Leone | |
| 5,728,131 A | 3/1998 | Frantzen | |
| 5,728,158 A | 3/1998 | Lau | |
| 5,733,303 A | 3/1998 | Israel et al. | |
| 5,735,892 A | 4/1998 | Myers | |
| 5,735,893 A | 4/1998 | Lau | |
| 5,741,327 A | 4/1998 | Frantzen | |
| 5,741,333 A | 4/1998 | Frid | |
| 5,746,691 A | 5/1998 | Frantzen | |
| 5,755,769 A | 5/1998 | Richard | |
| 5,755,773 A | 5/1998 | Evans et al. | |
| 5,755,778 A | 5/1998 | Kleshinski | |
| 5,766,151 A | 6/1998 | Valley et al. | |
| 5,766,238 A | 6/1998 | Lau | |
| 5,769,882 A | 6/1998 | Fogarty et al. | |
| 5,776,114 A | 7/1998 | Frantzen | |
| 5,776,161 A | 7/1998 | Globerman | |
| 5,782,907 A | 7/1998 | Frantzen | |
| 5,785,679 A | 7/1998 | Abolfathi et al. | |
| 5,788,626 A | 8/1998 | Thompson | |
| 5,797,953 A | 8/1998 | Tekulve | |
| 5,800,393 A | 9/1998 | Sahota | |
| 5,800,512 A | 9/1998 | Lentz et al. | |
| 5,800,514 A | 9/1998 | Nunez | |
| 5,800,525 A | 9/1998 | Bachinski | |
| 5,807,404 A | 9/1998 | Richter | |
| 5,810,872 A | 9/1998 | Kanesaka | |
| 5,824,036 A | 10/1998 | Lauterjung | |
| 5,824,037 A | 10/1998 | Fogarty et al. | |
| 5,824,040 A | 10/1998 | Cox | |
| 5,824,049 A | 10/1998 | Ragheb | |
| 5,824,054 A | 10/1998 | Khosravi et al. | |
| 5,824,056 A | 10/1998 | Rosenberg | |
| 5,827,321 A | 10/1998 | Roubin | |
| 5,836,966 A | 11/1998 | St. Germain | |
| 5,843,160 A | 12/1998 | Rhodes | |
| 5,843,175 A | 12/1998 | Frantzen | |
| 5,846,246 A | 12/1998 | Dirks | |
| 5,846,261 A | 12/1998 | Kotula et al. | |

(56) References Cited

U.S. PATENT DOCUMENTS

| | | | |
|---|---|---|---|
| 5,849,037 A | 12/1998 | Frid | |
| 5,860,998 A | 1/1999 | Robinson | |
| 5,863,627 A | 1/1999 | Szycher | |
| 5,867,762 A | 2/1999 | Rafferty et al. | |
| 5,868,708 A | 2/1999 | Hart | |
| 5,868,782 A | 2/1999 | Frantzen | |
| 5,871,537 A | 2/1999 | Holman | |
| 5,873,907 A | 2/1999 | Frantzen | |
| 5,876,448 A | 3/1999 | Thompson et al. | |
| 5,879,381 A | 3/1999 | Moriuchi | |
| 5,888,660 A | 3/1999 | Landoni et al. | |
| 5,902,332 A | 5/1999 | Schatz | |
| 5,919,224 A | 7/1999 | Thompson | |
| 5,928,279 A | 7/1999 | Shannon et al. | |
| 5,931,866 A | 8/1999 | Frantzen | |
| 5,944,750 A | 8/1999 | Tanner | |
| 5,947,991 A | 9/1999 | Cowan | |
| 5,948,184 A | 9/1999 | Frantzen | |
| 5,976,178 A | 11/1999 | Goldsteen et al. | |
| 5,984,955 A | 11/1999 | Wisselink | |
| 5,985,305 A * | 11/1999 | Peery et al. | 424/422 |
| 5,994,750 A | 11/1999 | Yagi | |
| 6,007,573 A | 12/1999 | Wallace | |
| 6,015,431 A | 1/2000 | Thornton | |
| 6,022,359 A | 2/2000 | Frantzen | |
| 6,033,434 A | 3/2000 | Borghi | |
| 6,042,606 A | 3/2000 | Frantzen | |
| 6,056,776 A | 5/2000 | Lau | |
| 6,066,167 A | 5/2000 | Lau | |
| 6,066,168 A | 5/2000 | Lau | |
| 6,083,259 A | 7/2000 | Frantzen | |
| 6,093,199 A | 7/2000 | Brown | |
| 6,099,548 A | 8/2000 | Taheri | |
| 6,110,198 A | 8/2000 | Fogarty et al. | |
| 6,123,715 A | 9/2000 | Amplatz | |
| 6,123,722 A | 9/2000 | Fogarty | |
| 6,124,523 A | 9/2000 | Banas et al. | |
| 6,132,457 A | 10/2000 | Chobotov | |
| 6,152,144 A | 11/2000 | Lesh | |
| 6,152,943 A * | 11/2000 | Sawhney | 606/193 |
| 6,168,592 B1 | 1/2001 | Kupiecki et al. | |
| 6,187,033 B1 | 2/2001 | Schmitt | |
| 6,187,034 B1 | 2/2001 | Frantzen | |
| 6,190,402 B1 | 2/2001 | Horton et al. | |
| 6,193,745 B1 | 2/2001 | Fogarty et al. | |
| 6,196,230 B1 | 3/2001 | Hall et al. | |
| 6,203,732 B1 | 3/2001 | Clubb | |
| 6,214,022 B1 | 4/2001 | Taylor et al. | |
| 6,231,562 B1 | 5/2001 | Khosravi et al. | |
| 6,235,050 B1 | 5/2001 | Quiachon et al. | |
| 6,241,761 B1 | 6/2001 | Villafana | |
| 6,254,633 B1 | 7/2001 | Pinchuk et al. | |
| 6,261,305 B1 | 7/2001 | Marotta et al. | |
| 6,280,466 B1 | 8/2001 | Kugler | |
| 6,283,991 B1 | 9/2001 | Cox et al. | |
| 6,290,722 B1 | 9/2001 | Wang | |
| 6,290,731 B1 | 9/2001 | Solovay et al. | |
| 6,296,603 B1 | 10/2001 | Turnlund et al. | |
| 6,299,597 B1 | 10/2001 | Buscemi et al. | |
| 6,299,604 B1 | 10/2001 | Ragheb | |
| 6,312,462 B1 | 11/2001 | McDermott et al. | |
| 6,312,463 B1 | 11/2001 | Rourke et al. | |
| 6,325,816 B1 | 12/2001 | Fulton, III | |
| 6,325,819 B1 | 12/2001 | Pavcnik et al. | |
| 6,331,184 B1 | 12/2001 | Abrams | |
| 6,331,191 B1 | 12/2001 | Chobotov | |
| 6,334,869 B1 | 1/2002 | Leonhardt et al. | |
| 6,344,056 B1 | 2/2002 | Dehdashtian | |
| 6,375,675 B2 | 4/2002 | Dehdashtian et al. | |
| 6,395,019 B2 | 5/2002 | Chobotov | |
| 6,409,757 B1 | 6/2002 | Trout, III et al. | |
| 6,432,131 B1 | 8/2002 | Ravenscroft | |
| 6,451,047 B2 | 9/2002 | McCrea | |
| 6,463,317 B1 | 10/2002 | Kucharczyk et al. | |
| 6,506,204 B2 | 1/2003 | Mazzocchi | |
| 6,527,799 B2 | 3/2003 | Shanley | |
| 6,544,208 B2 * | 4/2003 | Ethier et al. | 604/8 |
| 6,544,276 B1 | 4/2003 | Azizi | |
| 6,547,804 B2 | 4/2003 | Porter et al. | |
| 6,554,858 B2 | 4/2003 | Dereume et al. | |
| 6,576,007 B2 | 6/2003 | Dehdashtian et al. | |
| 6,579,301 B1 | 6/2003 | Bales | |
| 6,592,614 B2 | 7/2003 | Lenker et al. | |
| 6,613,037 B2 | 9/2003 | Khosravi et al. | |
| 6,645,242 B1 | 11/2003 | Quinn | |
| 6,656,214 B1 | 12/2003 | Fogarty et al. | |
| 6,656,220 B1 | 12/2003 | Gomez et al. | |
| 6,663,607 B2 | 12/2003 | Slaikeu et al. | |
| 6,663,667 B2 | 12/2003 | Dehdashtian et al. | |
| 6,679,300 B1 | 1/2004 | Sommer et al. | |
| 6,682,546 B2 | 1/2004 | Amplatz | |
| 6,692,486 B2 | 2/2004 | Jaafar et al. | |
| 6,692,528 B2 * | 2/2004 | Ward et al. | 623/17.12 |
| 6,695,833 B1 | 2/2004 | Frantzen | |
| 6,729,356 B1 | 5/2004 | Baker et al. | |
| 6,730,119 B1 | 5/2004 | Smalling | |
| 6,733,521 B2 | 5/2004 | Chobotov | |
| 6,761,733 B2 | 7/2004 | Chobotov | |
| 6,773,454 B2 | 8/2004 | Wholey et al. | |
| 6,776,771 B2 | 8/2004 | Van Moorlegem et al. | |
| 6,827,735 B2 | 12/2004 | Greenberg | |
| 6,843,803 B2 | 1/2005 | Ryan et al. | |
| 6,878,161 B2 | 4/2005 | Lenker | |
| 6,878,164 B2 | 4/2005 | Kujawski | |
| 6,887,268 B2 | 5/2005 | Butaric et al. | |
| 6,918,926 B2 | 7/2005 | Letort | |
| 6,945,989 B1 | 9/2005 | Betelia et al. | |
| 6,958,051 B2 | 10/2005 | Hart et al. | |
| 6,960,227 B2 | 11/2005 | Jones et al. | |
| 7,022,100 B1 | 4/2006 | Aboul-Hosn et al. | |
| 7,037,344 B2 * | 5/2006 | Kagan et al. | 623/23.65 |
| 7,105,012 B2 | 9/2006 | Trout, III | |
| 7,112,217 B1 | 9/2006 | Kugler | |
| 7,122,052 B2 | 10/2006 | Greenhalgh | |
| 7,131,991 B2 | 11/2006 | Zarins et al. | |
| 7,147,661 B2 | 12/2006 | Chobotov et al. | |
| 7,156,877 B2 * | 1/2007 | Lotz et al. | 623/17.16 |
| 7,175,651 B2 | 2/2007 | Kerr | |
| 7,229,472 B2 | 6/2007 | DePalma et al. | |
| 7,314,483 B2 | 1/2008 | Landau et al. | |
| 7,326,237 B2 | 2/2008 | Depalma et al. | |
| 7,435,253 B1 | 10/2008 | Hartley et al. | |
| 7,530,988 B2 * | 5/2009 | Evans et al. | 606/195 |
| 7,641,691 B2 * | 1/2010 | Lotz et al. | 623/17.12 |
| 7,666,220 B2 | 2/2010 | Evans et al. | |
| 7,682,383 B2 | 3/2010 | Robin | |
| 7,708,773 B2 | 5/2010 | Pinchuk et al. | |
| 7,789,911 B2 * | 9/2010 | Hamilton | 623/8 |
| 7,790,273 B2 | 9/2010 | Lee et al. | |
| 7,794,447 B2 * | 9/2010 | Dann et al. | 604/516 |
| 7,828,838 B2 | 11/2010 | Bolduc et al. | |
| 7,892,214 B2 * | 2/2011 | Kagan et al. | 604/264 |
| 7,951,448 B2 | 5/2011 | Lee et al. | |
| 8,088,162 B1 * | 1/2012 | Gieseke et al. | 623/14.13 |
| 8,292,911 B2 * | 10/2012 | Brister et al. | 606/192 |
| 8,545,530 B2 * | 10/2013 | Eskridge et al. | 606/191 |
| 2001/0020184 A1 | 9/2001 | Dehdashtian et al. | |
| 2001/0027337 A1 | 10/2001 | Robin | |
| 2001/0027338 A1 | 10/2001 | Greenberg | |
| 2001/0044655 A1 | 11/2001 | Patnaik et al. | |
| 2002/0019665 A1 | 2/2002 | Dehdashtian et al. | |
| 2002/0026217 A1 | 2/2002 | Baker et al. | |
| 2002/0045848 A1 | 4/2002 | Jaafar et al. | |
| 2002/0045931 A1 | 4/2002 | Sogard et al. | |
| 2002/0052643 A1 | 5/2002 | Wholey et al. | |
| 2002/0077594 A1 | 6/2002 | Chien et al. | |
| 2002/0151953 A1 | 10/2002 | Chobotov | |
| 2002/0151956 A1 | 10/2002 | Chobotov | |
| 2002/0151958 A1 | 10/2002 | Chuter | |
| 2002/0156518 A1 | 10/2002 | Tehrani | |
| 2002/0165521 A1 | 11/2002 | Cioanta et al. | |
| 2002/0169497 A1 | 11/2002 | Wholey et al. | |
| 2002/0183629 A1 | 12/2002 | Fitz | |
| 2003/0004560 A1 | 1/2003 | Chobotov | |

(56) References Cited

U.S. PATENT DOCUMENTS

| | | |
|---|---|---|
| 2003/0009132 A1 | 1/2003 | Schwartz et al. |
| 2003/0014075 A1 | 1/2003 | Rosenbluth et al. |
| 2003/0028209 A1* | 2/2003 | Teoh et al. .............. 606/191 |
| 2003/0036745 A1 | 2/2003 | Khosravi et al. |
| 2003/0040800 A1* | 2/2003 | Li et al. ................. 623/17.12 |
| 2003/0051735 A1 | 3/2003 | Pavcnik et al. |
| 2003/0074056 A1 | 4/2003 | Killion et al. |
| 2003/0078647 A1 | 4/2003 | Vallana et al. |
| 2003/0093145 A1 | 5/2003 | Lawrence-Brown et al. |
| 2003/0130720 A1 | 7/2003 | DePalma et al. |
| 2003/0130725 A1 | 7/2003 | DePalma et al. |
| 2003/0135269 A1 | 7/2003 | Swanstrom |
| 2003/0204242 A1 | 10/2003 | Zarins et al. |
| 2003/0204249 A1 | 10/2003 | Letort |
| 2003/0216802 A1 | 11/2003 | Chobotov et al. |
| 2003/0220649 A1 | 11/2003 | Bao et al. |
| 2004/0016997 A1 | 1/2004 | Ushio |
| 2004/0044358 A1 | 3/2004 | Khosravi et al. |
| 2004/0082989 A1 | 4/2004 | Cook et al. |
| 2004/0091543 A1 | 5/2004 | Bell et al. |
| 2004/0098096 A1 | 5/2004 | Eton |
| 2004/0116997 A1 | 6/2004 | Taylor et al. |
| 2004/0147811 A1 | 7/2004 | Diederich et al. |
| 2004/0153025 A1 | 8/2004 | Seifert et al. |
| 2004/0167607 A1 | 8/2004 | Frantzen |
| 2004/0193245 A1 | 9/2004 | Deem et al. |
| 2004/0204755 A1 | 10/2004 | Robin |
| 2004/0215172 A1 | 10/2004 | Chu et al. |
| 2004/0215316 A1 | 10/2004 | Smalling |
| 2004/0220522 A1 | 11/2004 | Briscoe et al. |
| 2004/0220669 A1* | 11/2004 | Studer ..................... 623/17.12 |
| 2004/0243057 A1 | 12/2004 | Vinten-Johansen et al. |
| 2005/0004660 A1 | 1/2005 | Rosenbluth et al. |
| 2005/0027238 A1 | 2/2005 | Fago et al. |
| 2005/0028484 A1 | 2/2005 | Littlewood |
| 2005/0065592 A1 | 3/2005 | Holzer |
| 2005/0085916 A1* | 4/2005 | Li et al. ................... 623/17.16 |
| 2005/0090804 A1 | 4/2005 | Chobotov et al. |
| 2005/0096731 A1 | 5/2005 | Looi et al. |
| 2005/0113929 A1* | 5/2005 | Cragg et al. .............. 623/17.16 |
| 2005/0215989 A1 | 9/2005 | Abboud et al. |
| 2005/0245891 A1 | 11/2005 | McCormick et al. |
| 2005/0251251 A1 | 11/2005 | Cribier |
| 2006/0015173 A1 | 1/2006 | Clifford et al. |
| 2006/0025853 A1 | 2/2006 | Evans et al. |
| 2006/0074481 A1 | 4/2006 | Vardi et al. |
| 2006/0135942 A1 | 6/2006 | Fernandes et al. |
| 2006/0142836 A1 | 6/2006 | Hartley et al. |
| 2006/0155369 A1 | 7/2006 | Edwin et al. |
| 2006/0161244 A1 | 7/2006 | Seguin |
| 2006/0184109 A1 | 8/2006 | Gobel |
| 2006/0206197 A1 | 9/2006 | Morsi |
| 2006/0212112 A1 | 9/2006 | Evans et al. |
| 2006/0265043 A1* | 11/2006 | Mandrusov et al. ......... 623/1.11 |
| 2006/0292206 A1 | 12/2006 | Kim et al. |
| 2007/0032850 A1 | 2/2007 | Ruiz et al. |
| 2007/0043420 A1 | 2/2007 | Lostetter |
| 2007/0050008 A1 | 3/2007 | Kim et al. |
| 2007/0055355 A1 | 3/2007 | Kim et al. |
| 2007/0061005 A1 | 3/2007 | Kim et al. |
| 2007/0150041 A1 | 6/2007 | Evans et al. |
| 2007/0162109 A1 | 7/2007 | Davila et al. |
| 2007/0208416 A1 | 9/2007 | Burpee et al. |
| 2007/0276477 A1 | 11/2007 | Lee et al. |
| 2008/0039923 A1 | 2/2008 | Taylor et al. |
| 2008/0154368 A1 | 6/2008 | Justis et al. |
| 2008/0228259 A1* | 9/2008 | Chu ........................... 623/1.11 |
| 2008/0294237 A1* | 11/2008 | Chu ........................... 623/1.15 |
| 2009/0099649 A1 | 4/2009 | Chobotov et al. |
| 2009/0198267 A1 | 8/2009 | Evans et al. |
| 2009/0209855 A1 | 8/2009 | Drilling et al. |
| 2009/0216125 A1 | 8/2009 | Lenker |
| 2009/0318949 A1 | 12/2009 | Ganpath et al. |
| 2009/0319029 A1 | 12/2009 | Evans et al. |
| 2010/0004728 A1 | 1/2010 | Rao et al. |
| 2010/0036360 A1 | 2/2010 | Herbowy et al. |
| 2010/0106087 A1 | 4/2010 | Evans et al. |
| 2010/0217383 A1 | 8/2010 | Leonhardt et al. |
| 2012/0016456 A1 | 1/2012 | Herbowy et al. |

FOREIGN PATENT DOCUMENTS

| | | |
|---|---|---|
| EP | 1325717 | 7/2003 |
| EP | 1903985 | 3/2010 |
| FR | 2834199 A1 | 7/2003 |
| JP | 2003-525692 A | 9/2003 |
| JP | 2004-537353 A | 12/2004 |
| JP | 2005-505380 A | 2/2005 |
| JP | 2005-532120 A | 10/2005 |
| JP | 2008-510502 A | 4/2008 |
| WO | 97/19653 | 6/1997 |
| WO | 98/53761 A1 | 12/1998 |
| WO | 00/29060 A2 | 5/2000 |
| WO | 00/51522 | 9/2000 |
| WO | 01/21108 | 3/2001 |
| WO | 01/66038 | 9/2001 |
| WO | 02/078569 A2 | 10/2002 |
| WO | 02/083038 A2 | 10/2002 |
| WO | 02/102282 | 12/2002 |
| WO | 03/007785 | 1/2003 |
| WO | 03/032869 A1 | 4/2003 |
| WO | 03/037222 A2 | 5/2003 |
| WO | 03/053288 A1 | 7/2003 |
| WO | 2004/004603 | 1/2004 |
| WO | 2004/026183 A2 | 4/2004 |
| WO | 2004/026183 A3 | 4/2004 |
| WO | 2004/037116 A2 | 5/2004 |
| WO | 2004/037116 A3 | 5/2004 |
| WO | 2004/045393 A2 | 6/2004 |
| WO | 2006/012567 A2 | 2/2006 |
| WO | 2006/012567 A3 | 2/2006 |
| WO | 2006/116725 A2 | 11/2006 |
| WO | 2007/008600 A2 | 1/2007 |
| WO | 2007/142916 A2 | 12/2007 |

OTHER PUBLICATIONS

Journal of Endovascular Therapy; Apr. 2000; pp. 111, 114, 132-140; vol. 7' No. 2; International Society of Endovascular Specialists; Phoenix, AZ.

Gilling-Smith, "Stent Graft Migration After Endovascular Aneurysm Repair," presented at 25th International Charing Cross Symposium, Apr. 13, 2003 [Power Point Presentation and Transcript], 56 pages total.

Carmi et al., "Endovascular stent-graft adapted to the endoluminal environment: prototype of a new endoluminal approach," J Endovasc Ther. Jun. 2002;9(3):380-381.

Donayre et al., "Fillable Endovascular Aneurysm Repair," Endovascular Today, pp. 64-66, Jan. 2009.

William Tanski, Mark Fillinger. *Outcomes of original and low-permeability Gore Excluder endoprosthesis for endovascular abdominal aortic aneurysm repair*. Journal of Vascular Surgery. Feb. 2007. p. 243-249.

Susan M. Trocciola et al. The development of endotension is associated with increased transmission of pressure and serous components in porous expanded polytetrafluoroethylene stent-grafts: Characterization using a canine model. Journal of Vascular Surgery. Jan. 2006. p. 109-116.

Shan-e-ali Haider et al. Sac behavior after aneurysm treatment with the Gore Excluder low-permeability aortic endoprosthesis: 12-month comparison to the original Excluder device. Journal of Vascular Surgery. vol. 44, No. 4. 694-700. Oct. 2006.

International Search Report and Written Opinion of PCT Application No. PCT/US2009/046310, dated Jul. 29, 2009, 9 pages total.

International Search Report of PCT/US 06/16403, dated Aug. 7, 2007. 2 pages.

International Search Report and Written Opinion of PCT Application No. PCT/US2006/062257, mailed Jan. 18, 2008. 7 pages total.

International Search Report and Written Opinion of PCT Application No. PCT/US07/69671, dated Jul. 7, 2008, 9 pages.

(56) References Cited

OTHER PUBLICATIONS

International Search Report and Written Opinion of PCT Application No. PCT/US09/34136, D dated Apr. 8, 2009, 16 pages total.
U.S. Appl. No. 12/371,087, filed Feb. 13, 2009, first named inventor: K.T. Venkateswara Rao.
International Search Report and Written Opinion of PCT Application No. PCT/US09/41718, dated Jun. 22, 2009, 23 pages total.
Supplementary European Search Report and Search Opinion of EP Patent Application No. 05773726, mailed Apr. 23, 2010, 6 pages total.
International Search Report and The Written Opinion of The International Searching Authority, Issued in PCT/US2012/032612 on Jul. 25, 2012, 13 pages.
The International Search Report of the International Searching Authority for Application No. PCT/US2012/021878, mailed on May 23, 2012, 4 pages.
The Written Opinion, including the search, of the International Searching Authority for Application No. PCT/US2012/021878, mailed May 23, 2012, 9 pages.
Extended European search report of corresponding EP Application No. 06751879.5, dated Apr. 16, 2013. 9 pages.
European Search Report and Search Opinion of EP Patent Application No. 06774540.6, mailed Mar. 30, 2010, 6 pages total.
EP report, dated Nov. 7, 2013, of corresponding EP Application No. 09733719.0.
Search report dated Oct. 17, 2013 of corresponding PCT/US2012/032612.
International Preliminary Report on Patentability PCT/US2012/021878 dated Aug. 1, 2013.
Report of European Patent Application No. 06850439.8 dated May 15, 2013.
Report for European Patent Application No. 06850439.8, May 15, 2013.
Examination report for JP Application. No. 2008-547709 dated Dec. 13, 2011.
International Search Report and Written Opinion of PCT Application No. PCT /US2009/046308, mailed Nov. 17, 2009, 12 pages total.
Examination Report of corresponding Japanese Application No. 2011-512667, dated Jun. 18, 2013.
International Preliminary Report on Patentability and Written Opinion of the International Searching Authority, Issued in PCT/US2010/061621 on Jul. 12, 2012, 7 pages.
PCT International Search Report and Written Opinion dated Feb. 28, 2011 for PCT Application No. PCT/US2010/61621. 11 pages.
U.S. Appl. No. 60/855,889, filed Oct. 31, 2006; first named inventor: Steven L. Herbowy.
U.S. Appl. No. 12/429,474, filed Apr. 24, 2009; first named inventor: Steven L. Herbowy.
U.S. Appl. No. 61/052,059, filed May 9, 2008; first named inventor: Gwendolyn A. Watanabe.
Search report of corresponding PCT/US2014/021928, mailed May 20, 2014. 8 pages.
Examination Report of Japanese Patent Application No. 2011-506487, dated May 7, 2014.

* cited by examiner

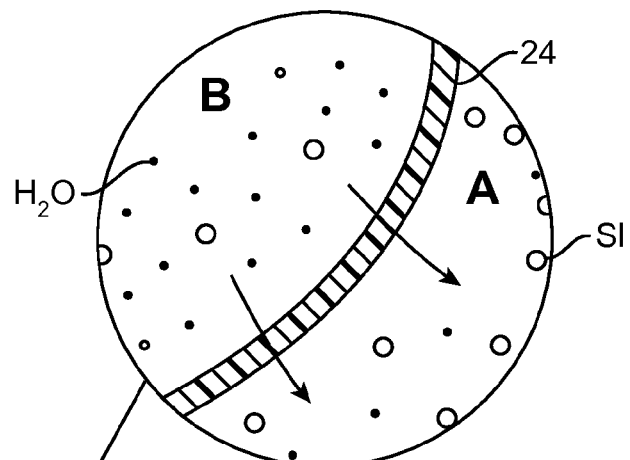
FIG. 3A-1
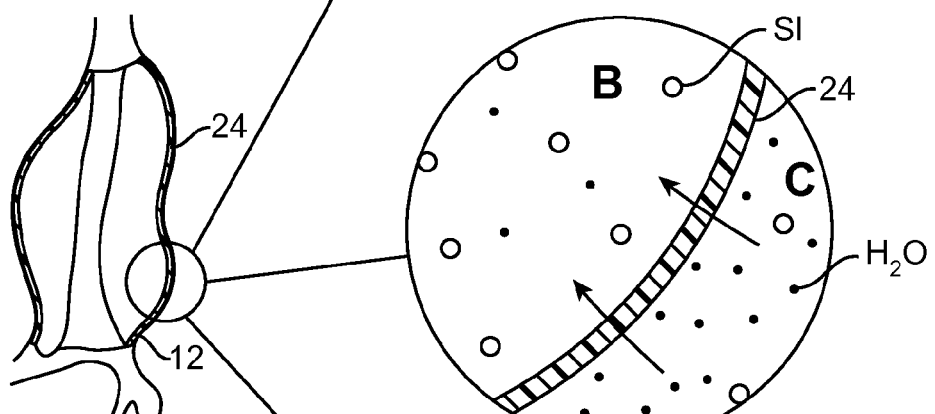
FIG. 3A
FIG. 3A-2
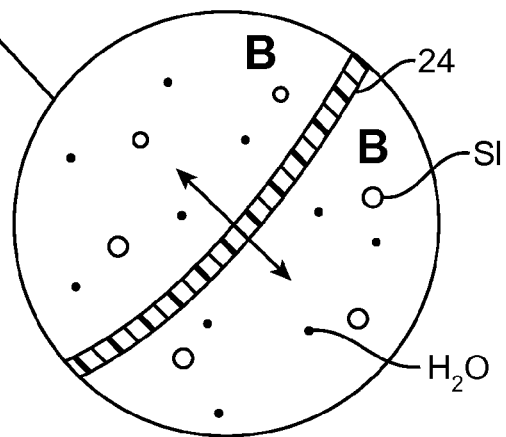
FIG. 3A-3

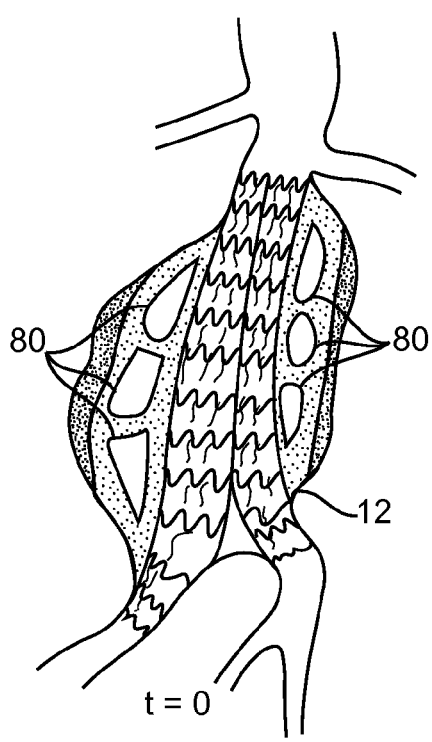
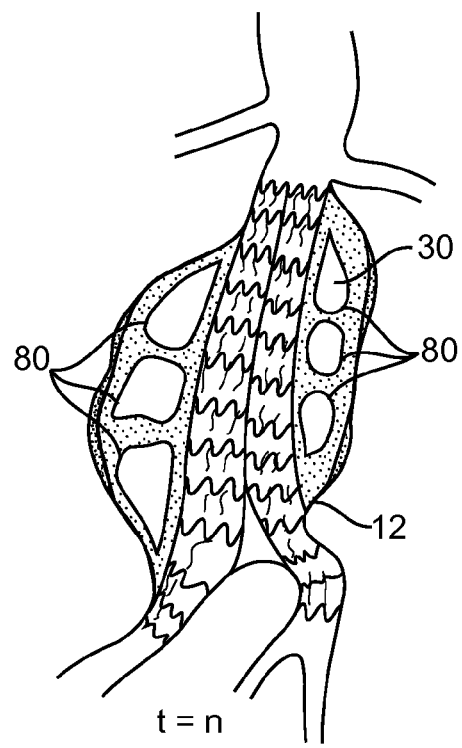
FIG. 8A FIG. 8B
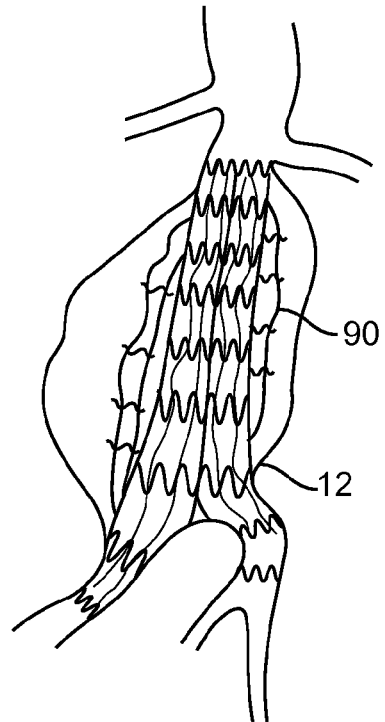
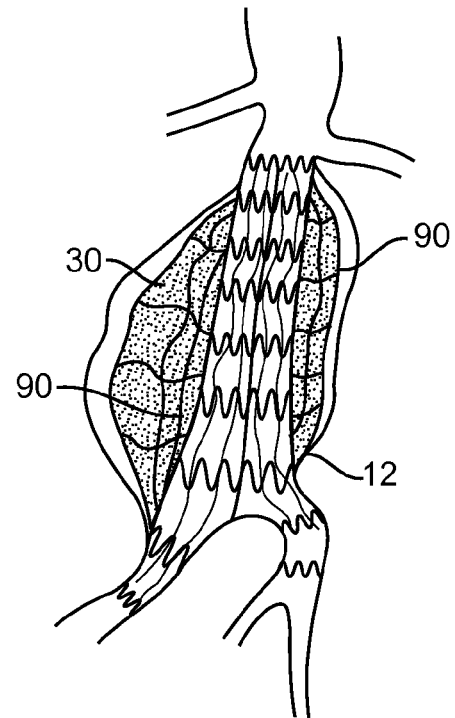
FIG. 9A FIG. 9B

GRAFT SYSTEMS HAVING SEMI-PERMEABLE FILLING STRUCTURES AND METHODS FOR THEIR USE

CROSS-REFERENCES TO RELATED APPLICATIONS

The present application is a non-provisional of, and claims the benefit of U.S. Provisional Patent Application No. 61/434,954, filed Jan. 21, 2011, the entire contents of which are incorporated herein by reference.

The present application is generally related to the following applications: U.S. application Ser. No. 11/187,471 now U.S. Pat. No. 7,530,988, filed on Jul. 22, 2005, U.S. application Ser. No. 11/413,460, filed on Apr. 28, 2006, provisional U.S. Application No. 60/589,850, filed on Jul. 22, 2004, provisional U.S. Application No. 60/675,158, filed on Apr. 28, 2005, and provisional U.S. Application No. 60/736,602, filed on Nov. 14, 2005, the full disclosures of which are incorporated herein by reference.

BACKGROUND OF THE INVENTION

1. Field of the Invention

The present invention relates generally to medical apparatus and methods for treatment. More particularly, the present invention relates to expandable prosthesis and methods for treating abdominal and other aneurysms.

Aneurysms are enlargements or "bulges" in blood vessels which are often prone to rupture and which therefore present a serious risk to the patient. Aneurysms may occur in any blood vessel but are of particular concern when they occur in the cerebral vasculature or the patient's aorta.

Of particular concern are aneurysms occurring in the aorta, particularly those referred to as aortic aneurysms. Aortic aneurysms are classified based on their location within the aorta as well as their shape and complexity. Abdominal aneurysms which are found below the renal arteries are referred to as infrarenal abdominal aortic aneurysms (AAAs). Suprarenal abdominal aortic aneurysms occur above the renal arteries, while thoracic aortic aneurysms (TAA's) occur in the ascending, transverse, or descending part of the upper aorta.

Infrarenal aneurysms are the most common, representing about seventy percent (70%) of all aortic aneurysms. Suprarenal aneurysms are less common, representing about 20% of the aortic aneurysms. Thoracic aortic aneurysms are the least common and often the most difficult to treat. Most or all present endovascular systems are also too large (above 12 F) for percutaneous introduction.

The most common form of aneurysm is "fusiform," where the enlargement extends about the entire aortic circumference. Less commonly, the aneurysms may be characterized by a bulge on one side of the blood vessel attached at a narrow neck. Thoracic aortic aneurysms are often dissecting aneurysms caused by hemorrhagic separation in the aortic wall, usually within the medial layer. The most common treatment for each of these types and forms of aneurysm is open surgical repair. Open surgical repair is quite successful in patients who are otherwise reasonably healthy and free from significant co-morbidities. Such open surgical procedures are problematic, however, since access to the abdominal and thoracic aortas is difficult to obtain and because the aorta must be clamped off, placing significant strain on the patient's heart.

Over the past decade, endoluminal repair has been used to treat aortic aneurysms in about 50% of the patients, especially for those patients who cannot undergo open surgical procedures. In general, endoluminal repairs access the aneurysm "endoluminally" through either or both iliac arteries in the groin. The grafts, which are generally made using fabric or membrane tubes supported and attached by various stent structures, are then implanted, typically requiring several pieces or modules to be assembled in situ. Successful endoluminal procedures have a much shorter recovery period than open surgical procedures.

Present endoluminal aortic aneurysm repairs, however, suffer from a number of limitations. A significant number of patients after endoluminal repair experience leakage at the proximal juncture (attachment point closest to the heart) within two years of the initial procedure. While such leaks can often be fixed by secondary interventional procedures, the need to have such follow-up treatments significantly increases cost and is certainly undesirable for the patient. A less common but more serious problem has been graft migration. In instances where the graft migrates or slips from its intended position, open surgical repair is required or may require the use of another extender graft.

A particularly promising endoluminal graft is described in U.S. Publication No. 2006/0025853, which corresponds to related application U.S. application Ser. No. 11/187,471, the full disclosure of which has previously been incorporated herein by reference. That patent application describes the treatment of the aortic and other aneurysms with a double-walled filling structure which is filled with a hardenable material and cured in situ. The structure conforms to the shape of the aneurismal space and resists migration and endoleaks. The particular design described, however, may in some situations have certain drawbacks. For example, after initial treatment and depressurization of the aneurysm with a graft system, the thrombus often resolves over time resulting in changes to the size and shape of the aneurysm sac. This may lead to leakage and loss of graft apposition to the inside surface of the aneurysm, formation of hygroma in the space between the graft and the aneurysm surface, and enlargement of the aneurysm, all of which can eventually lead to graft migration and/or repressurization of the aneurysm sac. A rigid endoluminal graft may not accommodate these morphological changes in size and/or shape of the aneurysm after endoluminal graft repair over time.

For these reasons, it would desirable to provide improved methods, systems, and prosthesis for the endoluminal treatment of aortic aneurysms. Such improved methods, systems, and treatments should preferably provide implanted prosthesis which result in minimal or no endoleaks, resist migration, are relatively easy to deploy, have a low introduction profile (preferably below 12 F), and can treat most or all aneurismal configurations, including short-neck and no-neck aneurysms as well as those with highly irregular and asymmetric geometries. Further it would be desirable to provide fillable aneurismal grafts having the capability to adapt and accommodate changes in the size and/or shape of the aneurysm and maintain the position of the device and graft apposition and seal against the inside surface of the aneurysm. At least some of these objectives will be met by the embodiments described hereinafter.

2. Description of the Background Art

Grafts and endografts having fillable components are described in U.S. Pat. Nos. 4,641,653; 5,530,528; 5,665,117; and 5,769,882; U.S. Patent Publications 2004/0016997; and PCT Publications WO 00/51522 and WO 01/66038. The following patents and published applications describe endofframes and grafts having cuffs, extenders, liners, and related structures: U.S. Pat. Nos. 6,918,926; 6,843,803; 6,663,667; 6,656,214; 6,592,614; 6,409,757; 6,334,869; 6,283,991; 6,193,745; 6,110,198; 5,994,750; 5,876,448; 5,824,037;

5,769,882; 5,693,088; and 4,728,328; and U.S. Published Application Nos. 2005/0028484; 2005/0065592; 2004/0082989; 2004/0044358; 2003/0216802; 2003/0204249; 2003/0204242; 2003/0135269; 2003/0130725; and 2002/0052643.

BRIEF SUMMARY OF THE INVENTION

Methods and systems for the endoluminal treatment of aneurysms, particularly aortic aneurysms including both abdominal aortic aneurysms (AAA's) and thoracic aortic aneurysms (TAA's) are provided. The systems include expandable prostheses having a fillable space and a membrane that allows fluid to permeate the membrane in the presence of a water potential differential. As used herein, fluid may refer to water molecules, including water molecules in a liquid or in a vapor, or fluid may refer to any water based fluids, such as a serum, or a fluid having therapeutic agents.

In a first aspect, the prostheses comprise double-walled filling structures which are pre-shaped and otherwise adapted to substantially fill the enlarged volume of an aneurysm, particularly a fusiform aneurysm, leaving a lumen in place for blood flow. The double-walled filling structure includes inner and outer walls and a fillable space therebetween. During deployment, the inner wall of the filling structure is expanded to define a generally tubular lumen for blood flow through the structure, while the outer wall of the filling structure expands to conform to the inside surface of the aneurysm, thereby excluding the aneurismal space from circulation. The inner wall is also designed to be impermeable to the transport of fluid filling media during the clinical procedure. The outer wall may be expanded against the inside surface of the aneurysm by filling the fillable space with a fluid filling medium so that the outer wall is in apposition with the aneurysm. After deployment, the membrane, preferably a semi-permeable membrane, allows transport of water molecules into or out of the fillable space through the membrane, the direction of fluid flow depending on the difference in water potential between the fillable space of the filling structure and the surrounding environment. The fillable space may be filled, at least partially, with a fluid filling medium, preferably a polymer hydrogel. The fluid filling medium may be selected so that the osmolarity of the filling medium induces an osmotic pressure within the filling structure sufficient to cause a desired osmotic pressure gradient across the membrane. Typically, the water molecules which permeate across the membrane into the fillable space will be from saline, serum or other body fluids. The overall water potential of the fluid within the fillable space will depend on the osmolarity of the fluid (which depends on the concentration of solutes in the fluid which are typically provided by the fluid filling medium), the pressure components, and gravimetric component and matrix effects, such as fluid cohesion and surface tension. The difference in water potential between the inside and outside of the filling structure causes transport of water molecules across the membrane. Transport of water molecules across the membrane into or out from the filling structure causes the filling structure to expand or contract, respectively, thereby accommodating changes in the size and/or shape of the aneurysm. In an embodiment, where the water potential differential is primarily caused by an osmotic gradient across the membrane, the membrane may comprise a semi-permeable membrane impermeable to at least one solute (the concentration of the solute inducing the osmotic gradient across the membrane). In some embodiments, the semi-permeable membrane may be less permeable or impermeable for a period of time after filling of the fillable structures, preferably within 24 hours of filling of the filling structure, to allow for changes in shape of the aneurysm due to depressurization after treatment. The membrane may be porous or non-porous. Typically, a non-porous membrane would be a semi-permeable membrane to allow diffusion of water vapor molecules through the membrane. Alternatively, the membrane may comprise pores which provide a mechanism for transport of fluid through the membrane in response to a water potential differential.

In another aspect, the outer or inner wall of the filling structure, or at least a portion thereof, may comprise the semi-permeable membrane. In some embodiments, the inner wall may comprise an impermeable material, while the outer wall may comprise a semi-permeable material. This prevents transport of fluid from the blood flowing through the generally tubular lumen across the membrane, while allowing for the flow of serum from the inside surface of the aneurysm and/or thrombus, promoting resolution or resorption of the thrombus and shrinkage of the aneurysm. The filling structures of the prosthesis will usually be formed from a non-compliant material, such as parylene, polyester (e.g., Dacron®), PET, PTFE, and/or a compliant material, such as silicone, polyurethane, latex, or combinations thereof. Usually, it is preferable to form at least the outer wall partially or entirely from a non-compliant material to enhance conformance of the outer wall to the inner surface of the aneurysm. This is particularly true when the aneurysm has been individually designed and/or sized for the patient being treated. The walls of the filling structure may be a polymer material, such as polyurethanes, including a non-porous ePTFE coated or rolled with polyurethane. The outer and/or inner walls of the filling structure may comprise ePTFE having an internodal distance ranging from 0.3 nanometers to 5 microns. The total thickness of the inner and/or outer walls may range from 20 µm to 120 µm, and are preferably about 40 µm. Water vapor permeability of the wall material may be within a range from about 0.01 to about 0.03 mL/day/cm$^2$, and is preferably about 0.015 mL/day/cm$^2$.

The fluid filling medium comprises one or more filling fluids, at least one of which may include a hardenable polymer. Preferably, the hardenable polymer comprises a hydrogel polymer, such as polyethylene glycol PEG. The filling medium may be selected so as to have an osmolarity (or dissolvable solutes for causing an osmolarity) to induce a desired water potential differential sufficient to cause permeation of water molecules across the membrane as needed to enlarge or shrink the filling structure to adjust for changes in the morphology of the aneurysm. The pressure within the filling structure may be controlled through selection of a filling medium which imparts a desired osmotic pressure to the fluid inside the fillable space (such as through dissolvable solutes in the fluid filling medium). By providing the necessary water potential in the filling structure, the permeation of water molecules through the membrane can be controlled to expand or contract the filling structure as needed. For example, providing a filling medium having a water potential lower than the surrounding environment outside the filling structure, such as a hydrophilic PEG having dissolvable solutes, causes fluid flow across the semi-permeable material into the filling structure, thereby enlarging the filling structure and increasing the pressure inside the filling structure until equilibrium is reached. Providing a filling medium having an osmolarity lower than the surrounding environment outside the filling structure causes fluid flow out from the filling structure, thereby shrinking the filling structure. By selectively expanding or contracting the filling structure, the system can accommodate changes in the size or shape of the aneurysm, maintain apposition of the filling structure with the inside surface of the aneurysm, and maintain a pressure inside the filling structure to adequately seal the aneurysm.

The double-walled filling structures will thus usually have a generally toroidal structure with an outer wall, an inner wall, and a fillable space or volume between the outer and inner walls to be filled with a filling medium. Filling of the fillable space expands the outer wall of the filling structure such that the outer surface of the outer wall conforms against an inside surface of the aneurysm. Filling of the fillable space also expands the inner wall of the filling structure such that an inner surface of the inner wall defines a generally tubular lumen which provides for blood flow after the prosthesis has been deployed. Typically, blood flowing through the generally tubular lumen is in direct contact with the inner surface of the inner wall. The shape of the filling structure will be preferably adapted to conform to the aneurysm being treated. The outer wall of the filling structure may be shaped to conform or be conformable to the inside surface of the aneurysm being treated. In some instances, the filling structure can be shaped for the aneurismal geometry of a particular patient using imaging and computer-aided design and fabrication techniques. In other instances, a family or collection of filling structures will be developed having different geometries and sizes so that a treating physician may select a specific filling structure to treat a particular patient based on the size and geometry of that patient's aneurysm.

The fillable space may be filled through a valve and a filling tube. The structure may include one or more filling tubes, such that the filling medium may be removed or additional medium may be added. In some embodiments, the fillable space comprises one or more chambers to control and/or limit flow fluid within the fillable space. The fillable space may be filled with one or more fluids, which may include saline, serum, or hardenable polymers. The fillable space may further include one or more semi-permeable bags; multiple semi-permeable bags may be in fluid communication with each other or may be independently filled. The semi-permeable bags may be filled with the filling medium or may expand to fill with fluid over time, such as fluid flowing into the structure through the semi-permeable material. In some embodiments, the filling structure may include a mesh within the fillable space to reinforce and secure the filling medium to the filling structure. The mesh may be attached to the inner wall so that the filling medium mechanically interlocks with the filling structure to provide support to the generally tubular lumen and secure the hardened filling medium to the filling structure, while still allowing the outer wall to expand.

The water potential of a fluid or the filling medium may be controlled by selecting (or by altering) the levels of dissolvable solutes within the fluid or medium. The water potential of fluid flowing into the structure may be controlled by using a filling medium having dissolvable solutes. In one aspect, the semi-permeable material will be permeable to water molecules so as to allow transport of fluid, such as water vapor, but impermeable to at least one solute, such that the concentration of the at least one solute causes a tonicity or an osmotic pressure differential across the semi-permeable membrane. In some embodiments, the semi-permeable material will allow transmission of at least some drugs or therapeutic agents.

In another aspect, the filling structure is oversized relative to the aneurysm, such that the total filling capacity of the filling structures is greater than the aneurismal space being treated. The oversized structure allows for expansion of the filling structure to accommodate an increase in available space inside the aneurysm as thrombus resorbs. In many embodiments, the outer wall of the filling structure may comprise folds which unfurl as the filling structure expands so as to maintain apposition between the outer wall and the inside surface of the aneurysm and to maintain an adequate pressure inside the filling structure to ensure an adequate seal between the filling structure and the inside surface of the aneurysm.

In addition to the filling structures just described, the aneurysm treatment systems may further include at least a first scaffold separate from the filling structure, where the scaffold can be expanded within or around the generally tubular lumen which provides the blood flow after the filling structure has been deployed in the aneurysm. The first scaffold will be adapted to expand within at least a first portion of the tubular lumen of the filling structure and may provide one or more specific advantages. For example, the scaffold may support and smooth the inside wall of the tubular lumen which in some cases might otherwise become uneven during hardening of the polymer fill. Scaffolds may also provide for anchoring of the filling structure, particularly at the aortic end of the graft when placed in an AAA. The scaffold may be partly or wholly covered with a membrane in order to form a graft. In such cases, the graft structure may help provide a transition from the blood vessel into the generally tubular lumen of the filling structure from the aortic end. Alternatively, the graft structure could provide one or a pair of transitions out of the iliac end of the filling structure. In a particular example, a graft structure can be used on either side of the filling structure in order to treat additional or continuing aneurismal regions in the adjacent blood vessel. In some embodiments, two or more filling structures may be used across the aneurysm. In such embodiments, a scaffold or multiple scaffolds may be placed within each filling structure.

Preferred delivery protocols for the filling structures will utilize delivery catheters having a balloon or other expandable support for carrying the filling structure. When using balloons, the balloons will preferably be substantially or entirely non-compliant, although compliant and combination compliant/non-compliant balloons may also find use. The balloon or other mechanical expansion components of the delivery catheter will initially be disposed within the inner tubular lumen of the filling structure, with the filling structure generally being collapsed into a low width or low profile configuration over the expansion element. The delivery catheter may then be introduced intraluminally, typically into the femoral artery and upwardly to the region within the aorta to be treated. The delivery catheter will also include one or more lumens, tubes, or other components or structures for delivering the filling medium in a fluid form to an internal filling cavity of the filling structure. Thus, the delivery catheter can be used to both initially place and locate the filling structure of the prosthesis at the aneurismal site. Once at the aneurismal site, the internal tubular lumen of the structure can be expanded using the balloon or other expandable element on the delivery catheter. The filling medium may be selected so that the medium has a quantity of dissolvable solutes sufficient to impart a concentration of solutes into the finable space so as to create the desired osmotic pressure in the fillable space. The membrane may be selected to allow transport of water molecules across the membrane to maintain a pressure inside the filling structure to adequately seal the aneurysm. The filling structure itself will be filled and expanded by delivering the filling medium via the catheter into the internal volume of the filling structure. Both expansion and filling operations may be performed simultaneously, or can be performed in either order, i.e. the filling structure may be filled first with the delivery catheter balloon being expanded second, or vice versa. The filling structure(s) and/or delivery balloons may have radiopaque markers to facilitate placement and/or pressure sensors for monitoring filling and inflation pressures during deployment. Once deployed, transport of water molecules through the semi-permeable material maintains the seal between the filling structure and the aneurysm, as well as the apposition of the outer wall to the inside surface of the aneurysm, expanding the outer wall outward when fluid flows into the filling structure and shrinking the structure when fluid flows out of the structure. This also helps to ensure that the filling structure is anchored in the aneurismal space, and does not migrate over time. In one aspect, the filling medium is selected so as to provide a salinity within the bag that is slightly above the high range of blood salinities that are likely to be experienced in the patient population so as to create an osmotic pressure (osmotic gradient) that is slightly positive. In another aspect, the osmotic pressure gradient provided is such that the bag does not shrink over time.

Delivery of a single prosthesis and filling structure to an aneurysm, as described thus far will be particularly suitable for aneurysms which are remote from a vessel bifurcation so that both ends of the filling structure are in communication with only a single blood vessel lumen. In the case of aneurysms located adjacent a vessel bifurcation, such as the most common, infrarenal abdominal aortic aneurysms, it will often be preferable to utilize two such filling structures introduced in a generally adjacent, parallel fashion within the aneurismal volume. In the specific case of the infrarenal aneurysms, each prosthesis will usually be delivered separately, one through each of the two iliac arteries. After locating the filling structures of the prosthesis within the aneurismal space, they can be filled simultaneously or sequentially to fill and occupy the entire aneurismal volume, leaving a pair of blood flow lumens.

In some embodiments, suitable filling materials will be fluid initially to permit delivery through the delivery catheter and will be curable or otherwise hardenable so that, once in place, the filling structure can be given a final shape which will remain after the delivery catheter is removed. The fillable materials will usually be curable polymers which, after curing, will have a fixed shape and hardness. The polymers may be delivered as liquids, gels, foams, slurries, or the like. In some instances, the polymers may be epoxies or other curable two-part systems. In other instances, the polymer may comprise a single material which, when exposed to the vascular environment within the filling structure, changes state over time, typically from zero to ten minutes.

In one aspect, after curing, the filling material will have a specific gravity, typically in the range from 0.1 to 5, more typically from 0.8 to 1.2 which is generally the same as blood or thrombus. The filling material may also include bulking and other agents to modify density, viscosity, mechanical characteristics or the like, including microspheres, fibers, powders, gasses, radiopaque materials, drugs, and the like. Exemplary filling materials include polyurethanes, collagen, polyethylene glycols, microspheres, and the like.

In view of the above general descriptions, the following specific embodiments may be better understood. In a first specific embodiment, methods for treating an aneurysm comprise positioning at least one double-walled filling structure across the aneurysm. By "across" the aneurysms, it is meant generally that the filling structure will extend axially from one anatomical location which has been identified by imaging or otherwise as the beginning of the aneurysm to a spaced apart location (or locations in the case of bifurcated aneurysm) where it has been established that the aneurysm ends. After positioning, the at least one filling structure is filled with a fluid filling medium so that an outer wall of the structure conforms to the inside of the aneurysm and an inner wall of the structure forms a generally tubular lumen to provide for blood flow after the filling structure has been deployed. Before the filling structure is being filled, while the filling structure is being filled, and after the filling structure has been filled, or during any one or more of these periods, the tubular lumen will preferably be supported, typically by a balloon or mechanically expansible element. After the filling structure has been filled, the filling material or medium is hardened while the tubular lumen remains supported. Supporting the tubular lumen during hardening assures that the lumen remains patent, will have a desired geometry, will properly align with adjacent vascular lumens and that the tubular lumen being formed remains aligned with the native aortic and/or iliac artery lumens after the prosthesis has been fully implanted. Preferably, the support will be provided by a balloon which extends proximally and distally of the filling structure where the balloon may slightly "overexpand" in order to assure the desired smooth transition and conformance of the tubular lumen provided by the filling structure with the native vessel lumens.

In a second specific embodiment, abdominal aortic aneurysms and other bifurcated aneurysms are treated by positioning first and second double-walled filling structures within the aneurismal volume. The first and second double-walled filling structures are positioned across the aneurysm, as defined above, extending from the aorta beneath the renal arteries to each of the iliac arteries, respectively. The first fluid filling structure is filled with a fluid filling material, the second filling structure is also filled with a fluid material, and the outer walls of each filling structure will conform to the inside surface of the aneurysm as well as to each other, thus providing a pair of tubular lumens for blood flow from the aorta to each of the iliac arteries. Preferably, the tubular lumens of each of the first and second filling structures are supported while they are being filled or after they have been filled. Further, the tubular lumens will preferably remain supported while the filling material is hardened, thus assuring that the transitions to the tubular lumens to the native vessel lumens remain properly aligned and conformed.

These and other embodiments are described in further detail in the following description related to the appended drawing figures.

BRIEF DESCRIPTION OF THE DRAWINGS

FIGS. 3A-3E illustrate various examples of transport of water molecules through the membrane in a fillable structure. FIG. 3A1-3A3 illustrate permeation of water molecules through the membrane in response to various water potential differentials between fluids inside and outside the fillable structure. FIGS. 3B-3C illustrate an embodiment wherein the permeation of water molecules expands the filling structure to accommodate an increase of the inner volume of the aneurysm that increases in size. FIGS. 3D-3E illustrate an embodiment wherein the transport of water molecules out of the filling structure contracts the filling structure to accommodate an aneurysm that decreases in size.

FIGS. 8A-8B illustrate an embodiment of the filling structure having multiple semi-permeable bags for accumulating or releasing water and/or serum from the inner space of the filling structure.

FIGS. 9A-9B illustrate an embodiment of the filling structure having a mesh for anchoring the filling medium to the inner wall of the filling structure.

DETAILED DESCRIPTION

Figure 1:
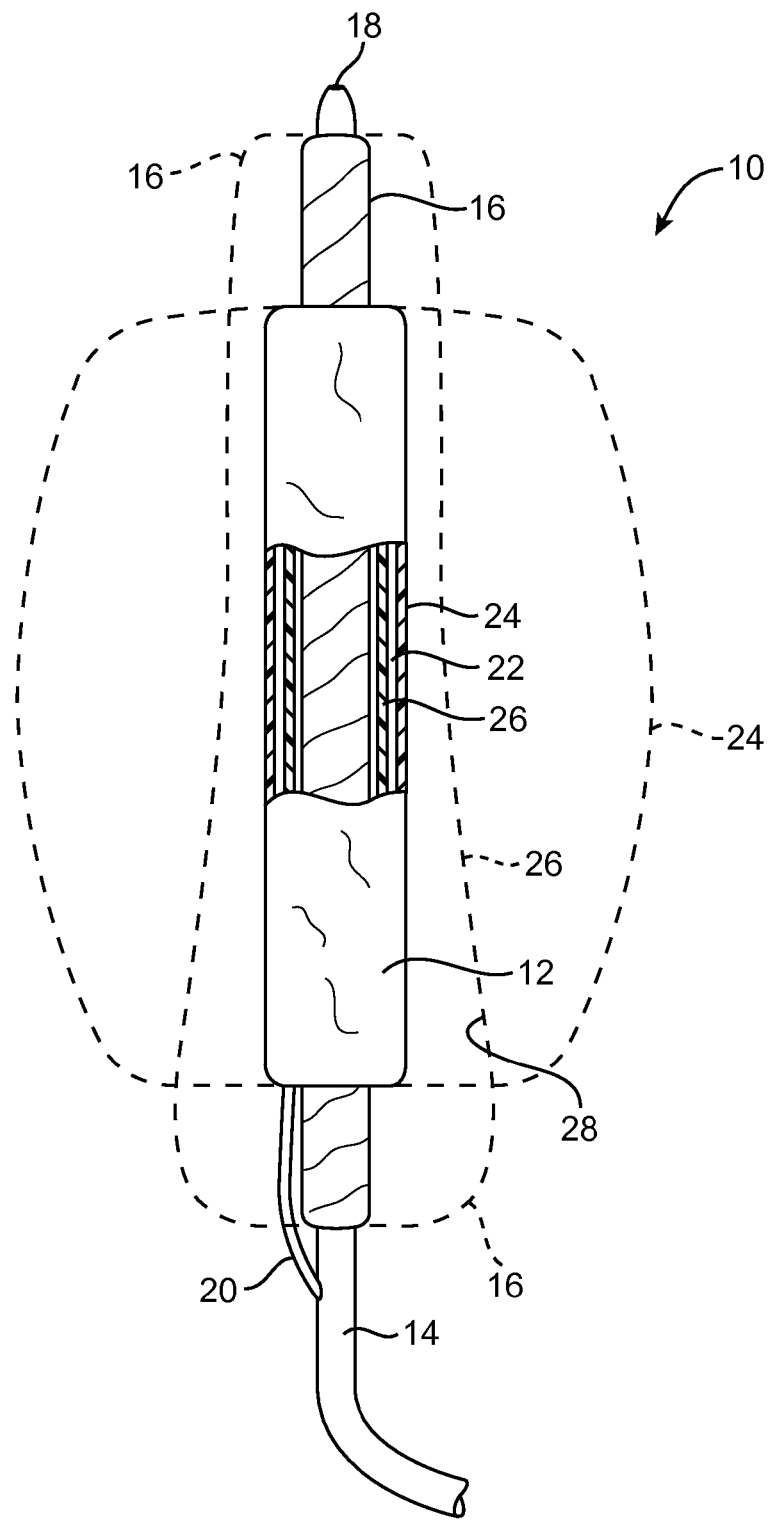
FIG. 1 illustrates a single filling structure having a semi-permeable material mounted over a delivery catheter.

Embodiments described relate to an aneurysm treatment system comprising a filling structure having a fillable space and a membrane that uses a water transport mechanisms, such as an osmosis process, to adjust the volume of fluid in the fillable space of the filling structure deployed in the aneurysm. By allowing the volume of a fillable space of the filling structure to increase (or decrease) through transport of a fluid through the membrane, such as by diffusion of water vapor through the membrane, the system may accommodate changes in the size or shape of the aneurysm over time. In a preferred embodiment, the water transport occurs through osmosis. In osmosis, which is sometimes referred to as "forward osmosis," a semi-permeable membrane is used to attract substantially pure water into a solution with a relatively high osmotic pressure from a solution having a relatively low osmotic pressure. In one embodiment, the fillable space of the filling structure is filled with a solution having an osmolarity sufficient to induce a desired osmotic pressure in the filling structure, the desired osmotic pressure slightly lower than the pressure outside the filling structure. Osmotic pressure exerted by a fluid is a function of the amount of dissolved solutes in the fluid, their molecular weight, and temperature and may be calculated by equations known to one of skill in the art. In a preferred embodiment, the osmolarity of the solution in the fillable space of the filling structure is controlled by the concentration of dissolvable solutes within the fluid filling medium which impart the desired osmolarity to the fillable space of the filling structure. Generally, as transport of a fluid, such as water vapor molecules, into the filling structure increases the solution within the fillable space, the dissolved solutes remain inside the fillable structure such that the osmolarity within the filling structure remain substantially constant over time. The transport of fluid into the filling structure through the membrane may be expressed as a flux rate, which may be selected by the physician as appropriate for individual treatment needs. The flux rate is caused primarily by the difference in osmotic pressure, the fluid transport properties of the membrane and the fluid pressure inside and outside of the filling structure. In a preferred embodiment, the transport of fluid occurs in response to an osmotic pressure differential and occurs through the diffusion of water vapor molecules through a semi-permeable membrane. One of skill in the art would appreciate that transport of fluid through the membrane may occur through various mechanisms, some of which are discussed in more detail below.

A system constructed in accordance with the principles described for treating an aneurysm in a blood vessel includes a filling structure having a fillable space and a membrane that allows fluid transport therethrough and a fluid filling medium for filling the filling structure. In a preferred embodiment, the membrane is a non-porous semi-permeable membrane through which fluid, such as water vapor molecules, diffuses into the fillable space of the filling structure. The fluid filling medium is selected to have an osmolarity to effect a desired osmotic pressure in the fillable space such that an increase in the volume of the aneurysm causes a water potential differential across the membrane such that fluid transport occurs into the filling structure. Preferably, the desired osmotic pressure is sufficient to maintain an adequate pressure inside the filling structure to seal the aneurysm and maintain the position of the filling structure in the aneurysm. In other embodiments, a difference in water potential may cause water molecules from fluids surrounding the filling structure, such as saline, serum and/or other body fluids, to permeate the semi-permeable membrane into the fillable space in response to the osmotic pressure differential until the water potential inside and outside the filling structure reaches equilibrium. By whichever mechanism water is transmitted across the membrane, the water will continue to flow toward the space having a lower water potential until equilibrium is reached. Factors affecting the equilibrium point include the difference in osmotic pressure, the internal pressure of the filling structure, as well as the pressure external of the filling structure. Hence, if the fillable inner space of the filling structure has a lower water potential than that of the external fluid surrounding the filling structure (such as when the aneurysm expands), then fluid will flow across the material into the fillable inner space causing the filling structure to expand until equilibrium is reached. If the fillable inner space has a water potential higher than the surrounding external fluid, the fluid will flow across the semi-permeable material from the fillable inner space causing the filing structure to shrink or contract until equilibrium is reached. Thus, the flux rate, or rate of fluid flow across the membrane, may be controlled through the selection of a membrane having certain fluid transport properties and the selection of a filling medium having dissolvable solutes sufficient to impart a desired osmotic pressure to the fillable space, thereby facilitating osmotic diffusion across the membrane when a water potential differential exists between the fillable space and the surroundings. It should be noted that generally fluid flow across the membrane does not include the fluid filling medium or the solutes affecting the osmolarity. For example, a semi-permeable membrane would be impermeable to the fluid filling medium, such as PEG. Even in an embodiment where the membrane is a porous material, the pores may be sized so as to allow transfer of fluid, but not the fluid filling medium.

The capability of the present system to expand and contract is advantageous as it allows the outer wall of the filling structure to accommodate changes in the volume and/or geometry of the aneurysm over time. Ideally, the outer wall of the filling structure is in apposition with the inside surface of the aneurysm and/or the vessel wall. Additionally, it may be desirable for the filling structure to be filled to a volume such that the filling structure exerts either a neutral pressure, or a slightly positive a pressure against the inside surface of the aneurysm. Preferably, the pressure exerted by the filling structure would be sufficient to maintain the position of the filling structure in the aneurysm and to maintain a seal between the filling structure and the vessel walls, thereby preventing or reducing flow of blood between the filling structure and the vessel walls. The pressure exerted against the vessel wall by the filling structure, however, should not be so large that the pressure would cause the aneurysm to grow. Once this optimal pressure is determined, the desired osmotic pressure at the equilibrium point can be determined, equilibrium being the point at which transport of fluid into (or out of) the filling structure ceases.

After initial treatment, the thrombus on the inside surface of an aneurysm may resolve due to depressurization of the aneurysm, which may result in an increase in the inner volume of the aneurysm. As the inner volume of the aneurysm increases, the outer wall of the filling structure may lose the seal between the filling structure and the aneurysm, potentially resulting in endoleaks or enlargement of the aneurysm. Mean changes in aneurysm size one year following treatment are typically less than 10 mm in aneurysm sac size diameter. However, even small changes in aneurysm sac size may result in the problems discussed above. Controlling transport of fluid, such as water molecules, into or out from the filling structure improves the ability of the filling structure to maintain a seal between the filling structure and the aneurysm, thereby reducing the likelihood of endoleaks, uncontrolled growth of the aneurysm, or migration of the implant.

In an exemplary embodiment, the membrane comprises a semi-permeable polyurethane, which may include polycarbonate and polyether urethanes. Typically, polyurethanes comprise segments cross-linked by semi-crystalline hard segments such that water molecules in an osmosis process permeate the polyurethane through the soft segments. The permeation of water molecules through the polyurethane is influenced by the chemical nature, morphology and spatial arrangement of the soft segments in the material. Although the equilibrium water content of polyurethane films may range from a few percent in volume to substantially more than 50% in volume, ideally the membrane comprises a polyurethane having a relatively low water content. In such an embodiment, it is believed that transport of water molecules through the membrane occurs through diffusive permeation of water vapor molecules across the membrane. This transport of water molecules across the membrane may be modeled as diffusion driven by differences in water vapor pressure on either side of the membrane. Diffusive permeation can be described by the following equations:

$$N = \frac{PA}{h} \Delta p_{H_2O} \quad (1)$$

$$\Delta p_{H_2O} = p_{H_2O,in} - p_{H_2O,out} \quad (2)$$

wherein in equation (1), N is the rate of water permeation, P is the diffusive permeability, which itself is the product of diffusivity times solubility, A is the mass transfer area, h is the membrane thickness, and $\Delta p_{H_2O}$ is calculated from equation (2), $\Delta p_{H_2O}$ being the difference in water partial pressure between the inside $p_{H_2O}$, in and outside $p_{H_2O}$, out surfaces of the membrane.

The difference in partial pressure between the inside and outside surfaces of the membrane may be controlled through the selection of the fluid filling medium, preferably a hydrophilic PEG having dissolvable solutes dispersed therein. Preferably, the PEG in the filled filling structure is kept moist such so that the PEG may affect the partial pressure or osmolarity of the solution in the fillable space through its dissolved solutes. Additionally, the PEG may exert an osmotic swelling pressure as water molecules are imbibed into the hydrogel (such osmotic swelling pressure may be modified by the presence of ions, such as when the hydrogel is charged). The osmotic swelling pressure is additive to the osmotic pressure created by the dissolved solutes in the solution within the fillable space. This gel osmotic pressure can be calculated for certain idealized system if the Flory Huggins parameter for the filling medium is known. The partial pressure of the water vapor in the filling structure may be estimated using Raoult's law or other equations associated with osmotic pressure, or water vapor partial pressure known to one of skill in the art. The claimed system is not limited by the above equations and alternatively, the water transport characteristics of the system could be determined empirically.

The membrane can be located anywhere on the filling structure so long as fluid can flow into or out from the fillable inner space of the filling structure. For example, the membrane may comprise a semi-permeable material incorporated into a portion of the inner or outer wall. Alternatively, the inner and/or outer wall may be constructed entirely from the semi-permeable material. The semi-permeable material may be used in combination with an expandable or over-sized filling structure so that flow of water into the filling structure expands the filling structure so as to maintain apposition with the aneurysm walls. Maintaining apposition between the filling structure and the aneurysm walls helps maintain the seals at either end of the device, reduce the likelihood of endoleaks due to changes in morphology of the aneurysm, anchor the prosthesis and prevent migration of the structure. The shape of the over-sized filling structure can be controlled and pre-planned to suit the aneurysm size based on the starting thrombus load to ensure that the bag will not expand the aneurysm due to excess transport of fluid into the filling structure.

Osmosis and reverse osmosis operate by a number of different transport mechanisms or theories. The mechanism by which the transport of water occurs across the membrane may depend on the chemical nature of the membrane being used as well as the molecule being transported through the membrane. Transport mechanisms known to one of skill in the art of osmosis and reverse osmosis include "solution-diffusion," convective flow, surface force-pore flow model, and the vapor pressure (or partial pressure) model. Depending on the Chemical composition and structure of the membrane used, the actual mechanism may be any of the transport mechanisms known to be operable for osmosis processes in general. In many embodiments, the membrane may comprise a polyurethane, in which the mechanism for transport of water molecules is believed to be a differential in vapor pressure. Where the membrane comprises materials other than polyurethane, the mechanism of transport is either known in the art to those skilled in osmosis and reverse osmosis membranes or would be readily determinable. Regardless of which transport mechanism causes the transport of water molecules across the membrane, however, the flux rate of water molecules across the membrane can be measured under simulated in-vivo conditions to determine the required transport characteristics of the structure without ever directly determining the transport mechanism. It should be noted that although the above described transport mechanisms are believed to be the predominate mechanisms by which transport may occur, the inventors do not intend to be bound by any particular theory.

Referring now to FIG. 1, the system may comprise a double-walled filling structure 12, at least a portion of which comprises the semi-permeable material. The filling structure 12 may be delivered to an aneurysm with a delivery catheter 14 having an expandable element 16, typically an inflatable balloon, at its distal end. The catheter 14 will comprise a guidewire lumen 18, a balloon inflation lumen (not illustrated) or other structure for expanding other expandable component's, and a filling tube 20 for delivering the filling medium or material to an internal space 22 of the double-walled filling structure 12. The internal space 22 is defined between an outer wall 24 and inner wall 26 of the filling structure. Upon inflation with the filling material or medium, the outer wall 24 will expand radially outwardly, as shown in broken line, so as to contact the inside surface of the vessel and/or the aneurismal space, while the inner wall 26 defines an internal lumen 28 to facilitate flow of blood through the filling structure. The expandable balloon or other structure 16 will be expandable to support an inner surface of the lumen 28, as also in broken line in FIG. 1. The internal space 22 is in fluid communication with an external environment surrounding the filling structure 12 through the semi-permeable material such that fluid can flow into or out from the internal space 22 thereby expanding or shrinking the filling structure, respectively, to accommodate changes in the morphology of the aneurysm.

Figure 2:
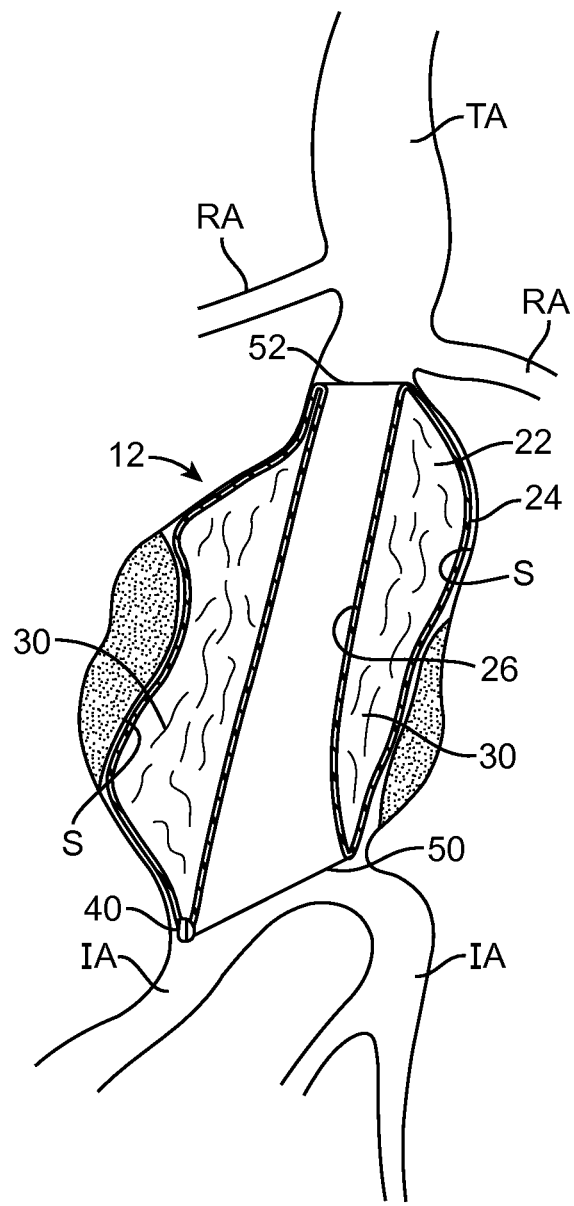
FIG. 2 is a cross-sectional view of a prosthesis system including a filling structure having a semi-permeable material and a filling medium.

Referring now to FIG. 2, the double-walled filling structure 12 will typically comprise at least one valve 40 to permit the introduction of the fluid filling medium 30 into the internal volume 22 through the filling tube 20. The valve 40 may be a simple flap valve. Other more complex ball valves, and other one-way valve structures may be provided. In other instances, two-way valve structures may be provided to permit both filling and selective emptying of the internal volume 22. In other instances, the filling tube may comprise a needle or other filling structure to pass through the valve 40 to permit both filling and removal of filling medium.

The wall structure of the double-walled filling structure may be a single layer, typically molded or otherwise conventionally formed. The wall structures may also be more complex and include multiple layers. It will be appreciated that such multiple layer structures can provide for increased strength, puncture resistance, variations in compliance and/or flexibility, differences in resistance to degradation, controlled porosity and the like. The semi-permeable material may be formed into at least a portion of the outer or inner wall. In many embodiments, the entire outer wall and inner wall comprises a semi-permeable membrane, such as ePTFE coated or laminated with polyurethane. Preferably, the filling structure is constructed such that the ePTFE is facing the outer blood contacting surface and the polyurethane is facing the inner non-blood contacting surface.

The system 10 further comprises a fluid filling medium. In a preferred embodiment, the fluid filling medium is hardenable so as to support the inner and outer wall in the expanded state. The fluid filling medium may also have an associated osmolarity such that fluid in contact or diffusing through the filling medium has substantially the same osmolarity as the filling medium. In a preferred embodiment, the fluid filling medium is hardenable and comprised of PEG, which is typically over 75% water even in the hardened state. The PEG may have a dissolvable solute such that fluid in contact with the PEG has substantially the same osmolarity as the PEG. For example, the filling medium may include a dissolvable solute, thereby causing the solutes to dissolve into any fluid within the fillable space. Alternatively, the filling structure may be filled with fluid having a different osmolarity than the fluid filling medium, or the solute may be added separately as a dissolvable solute. For example, the hardenable filling medium may be delivered to provide support for the filling structure, and then a fluid having the desired concentration of solutes may be delivered to the fillable space. In another aspect, the osmolarity of the fluid within the filling structure may be variable. For example, the dissolvable solutes may dissolve at a controlled rate as in a timed release.

In a preferred embodiment, the fluid filling medium provides the desired osmolarity. For example, the filling medium may comprise dissolvable solutes which dissolve into a fluid in contact with the medium. The osmolarity of the solution may be adjusted primarily through selection of materials having a specific osmolarity. In many embodiments, the osmolarity of the filling medium may range from 50 mOsm/L to 350 mOsm/L, and more preferably from 175 mOsm/L to 265 mOsm/L. Typically, the polymer will be hypertonic to saline and/or blood and will provide fluoroscopic visibility for monitoring the filling structure over time. In a preferred embodiment, the filling medium comprises a 1% RO PEG polymer hydrogel having an osmolarity of about 210 mOsm/L with a borderline hypertonicity to saline, a computed tomography (CT) density of 250 Hounsfield units (HU) and computed tomographic (CT) visibility. 1% RO refers to a formulation containing 1% by weight of a radiopaque salt incorporated in to the formulation, preferably sodium diatrizoate.

Referring now to FIG. 3A, the semi-permeable membrane may allow water molecules to cross the membrane in response to a water potential differential between fluids on opposing sides of the semi-permeable membrane. Water potential is the potential energy of water per unit volume relative to pure water in reference conditions. Water potential quantifies the tendency of fluid to move from one area to another due to osmosis, gravity, mechanical pressure, or matrix effects such as surface tension. If possible, water will move from an area of higher water potential to an area of lower water potential. The addition of solutes, for example, lowers the water potential of a fluid. The semi-permeable membrane is impermeable to a solute (SI) such that the solutes within the filling structure cause an inflow of fluid into the filling structure, thus creating an osmotic pressure. The osmotic pressure is the pressure applied by the fluid solution inside the filling structure to prevent the inward flow of water across the semi-permeable membrane. Providing a filling medium with a certain concentration of solutes induces an osmotic pressure within the filling structure thereby ensuring an adequate pressure inside the filling structure to maintain a seal against the inside surface of the aneurysm. A change in water potential across the membrane (such as from a decrease in fluid pressure in the filling structure caused by a slight increase in the aneurismal space) would cause fluid transfer across the membrane until an equilibrium in the water potential on opposing sides of the membrane was reached. Once equilibrium is reached, changes in the volume of the aneurysm over time would cause a loss of equilibrium and would cause a differential in water potential due to the change in pressure. The water potential differential, in turn, causing fluid inflow or outflow from the inner volume 22 of the filling structure, thereby enlarging or contracting the filling structure to accommodate changes in the morphology of the aneurysm until equilibrium is reached.

FIG. 3A1 depicts a hypertonic environment where the solute concentration (A) outside the filling structure is greater than the solute concentration (B) of the fluid inside the filling structure. The lower concentration of solutes in fluid within the filling structure results in a water potential that is higher than that of the body fluids external the filling structure. As a result, water molecules diffuse through the semi-permeable membrane of the outer wall 24 and flow out of the filling structure 12, thereby shrinking the internal volume. This aspect may be useful when a reduction in the overall volume of the filling structure is desired over time, such as when an aneurismal sac decreases in size after treatment until equilibrium is reached.

FIG. 3A2 depicts a hypotonic environment where the solute concentration (B) inside the filling structure is greater than the solute concentration of the fluid (C) outside the filling structure. The higher concentration of solutes inside the filling structure results in an osmolarity that is higher than that of body fluids external the filling structure. As a result, water molecules diffuse through the semi-permeable membrane of outer wall 24 and flow into the inner space 22 of filling structure 12, thereby expanding the filling structure or increasing the pressure inside the filling structure. This aspect may be useful when an increase in the overall volume of the filling structure is desired over time or a slight positive pressure is desired to maintain an adequate seal between the filling structure and the inside surface of the aneurysm.

FIG. 3A3 depicts an isotonic environment where the solute concentration of fluids (B) inside the filling structure is the same as that of fluid (B) outside the filling structure. Since the water potential of both fluids are about the same, water molecules flow into and out of the filling structure through the semi-permeable membrane of the outer wall 24 at approximately the same rate. This aspect may be useful when a filling structure of constant size is required, such as when the aneurysm and thrombus have stabilized and no change in the volume of the filling structure is desired.

Figure 3B:
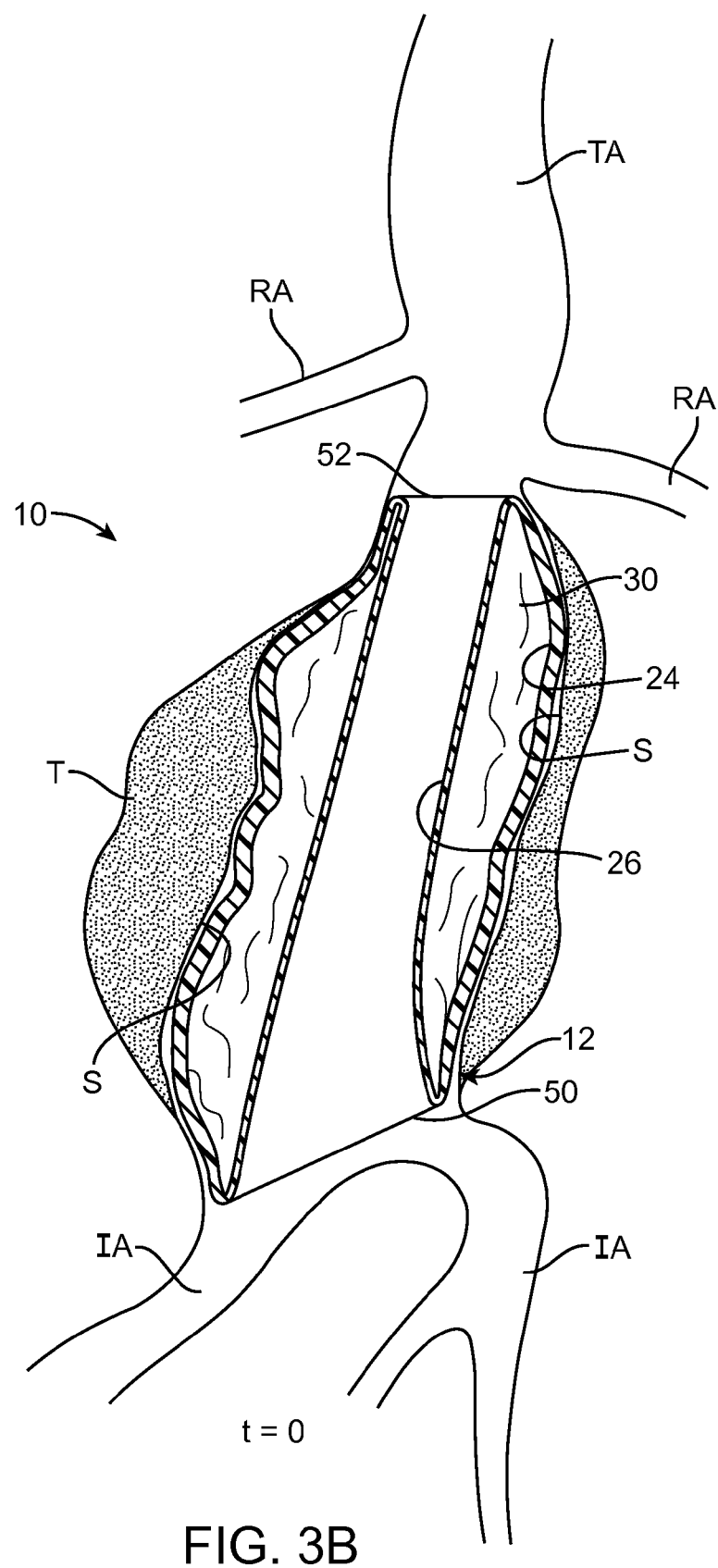

FIG. 3B depicts an embodiment comprising a double-walled filling structure 12 and a hardenable fluid filling medium 30 at the time of deployment (t=0). Upon deployment, the fillable inner space of the filling structure 12 is filled with the fluid filling medium 30 so that the outerwall 24 contacts the inside surface (S) of the aneurysm and the inner wall 26 defines a generally tubular lumen from upper opening 52 to lower opening 50. The inside surface S of the aneurysm may include the inside surface of the vessel wall as well as any thrombus or material disposed thereon. The filling medium 30 is then cured so as to support the generally tubular lumen, anchor the filling structure in the aorta and seal the filling structure against the inside surface S. In this embodiment, the filling medium 30 is a hardenable polymer hydrogel which contains dissolvable solutes such that the osmolarity of the filling medium is higher than that of fluid surrounding the filling structure. The outer wall 24 is in apposition with the aneurysm, such that outer wall 24 is substantially in surface contact with inside surface S.

Figure 3C:
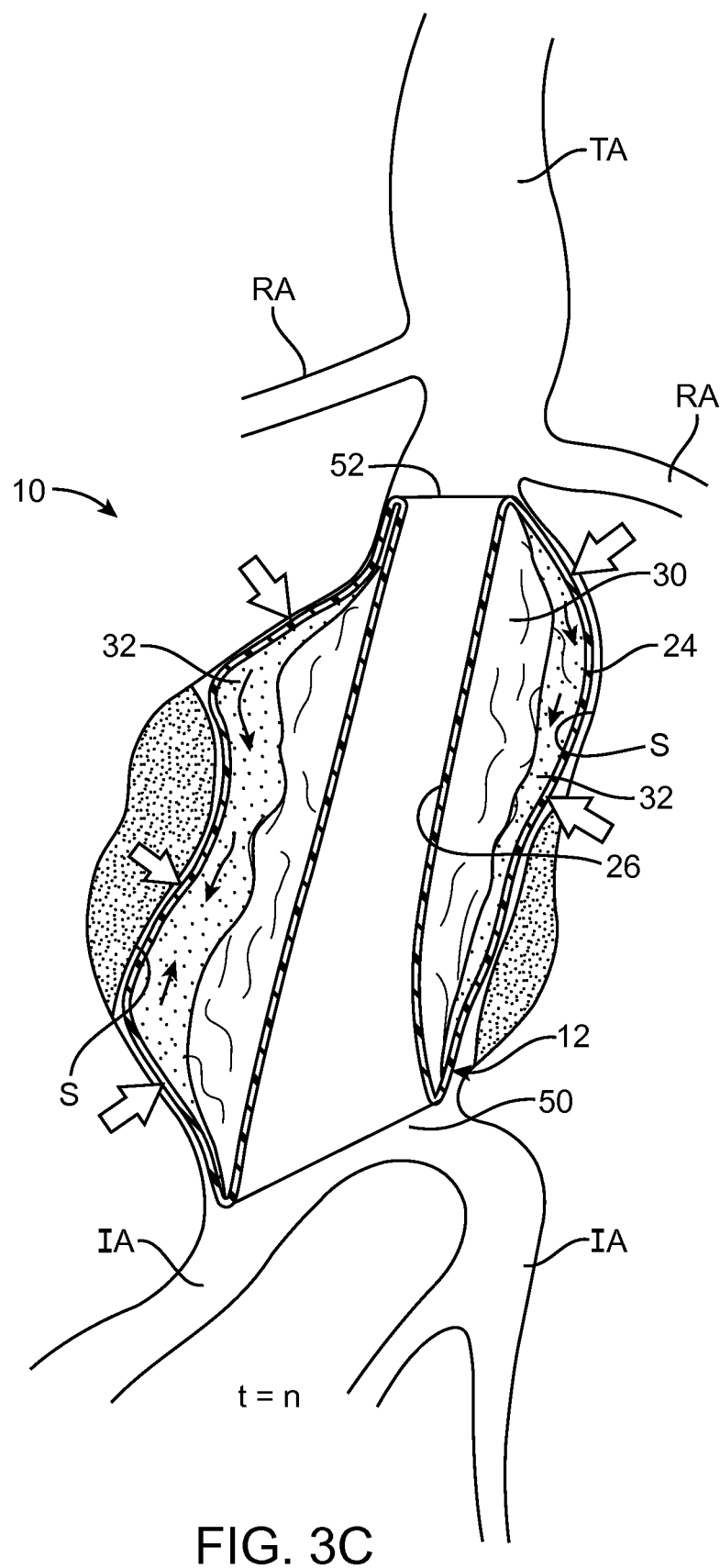

FIG. 3C depicts the embodiment of FIG. 3B at a later time after deployment (t=n, n>0) at which the aneurysm has been depressurized and the thrombus has resolved resulting in an increased inner volume of the aneurysm. The outer wall 24 is a semi-permeable material and allows transport of water molecules from the serum from the inside surface (S) of the aneurysm into the fillable space. Although the fillable medium 30 has been previously cured, the filling structure 12 is expandable so as to allow the flow of water molecules 32 into the fillable space (as shown by the arrows in FIG. 3C) expanding the outer wall 24 outward to maintain apposition of the filling structure with the inside surface S. While the cured fillable medium 30 maintains its shape at the time of deployment and continues to provide anchoring and support for the generally tubular lumen, the expansion of the outer wall 24 creates a layer of fluid within the filling structure 12 which further anchors and seals the filling structure by maintaining apposition of the outer wall 24 with the inside surface S of the aneurysm. In some embodiments, the semi-permeable membrane may be less permeable or impermeable to fluid for a period of time after initial filling of the filling structure, preferably within 24 hours. This may allow the aneurysm to change shape or size due to depressurization, after which the membrane may become semi-permeable to fluid allowing the bag to expand and fill subsequent enlargement of the aneurismal space due to thrombus resolution over time. This semi-permeable membrane having variable permeability may comprise PEG having a dissolvable or degradable polymer that once dissolves or degraded allows water-based fluids to permeate through the layer.

Figure 3E:
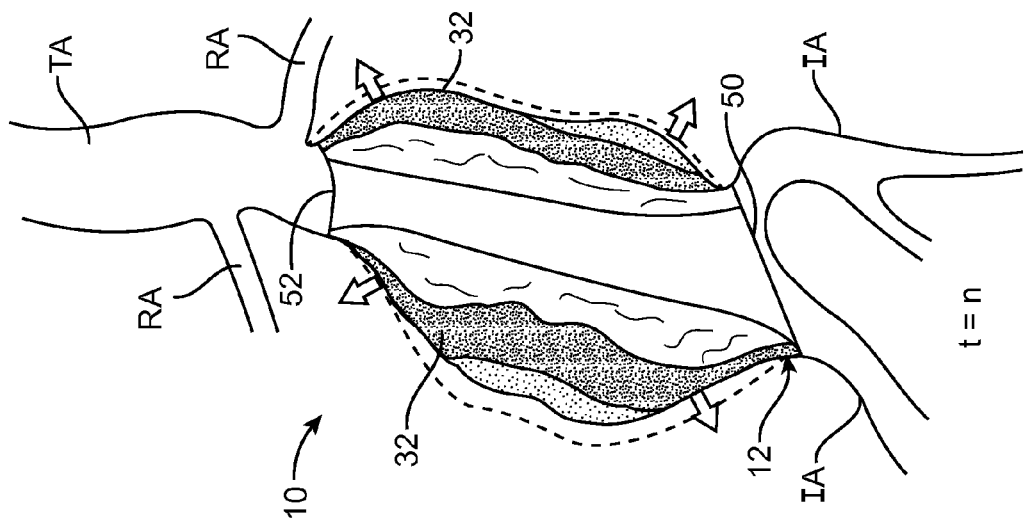
Figure 3D:
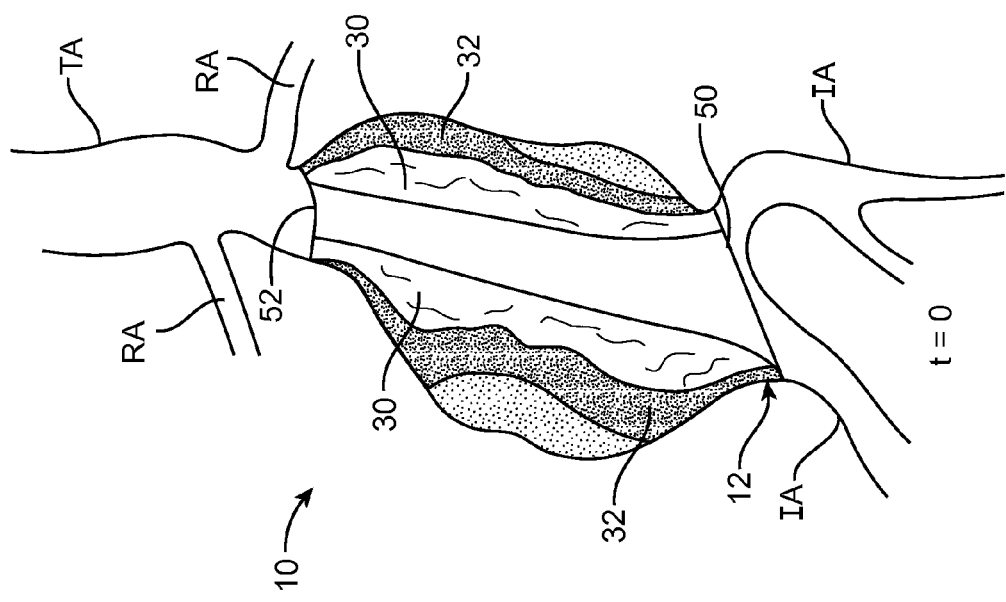

FIGS. 3D-3E depict an alternative embodiment wherein initially the filling structure comprises a filling medium comprising a hardenable polymer and fluid and/or saline. In this embodiment, the osmolarity of the filling medium is such that transport of fluid involves diffusion of water molecules out from the fillable space thereby contracting the filling structure 12 to accommodate a reduction in size of the aneurysm. Such an embodiment may include partially filling the fillable space with a hardenable polymer surrounding the generally tubular lumen and partially filling the fillable space with a fluid in contact with the outer wall 24 thereby allowing space for the outer wall 24 to contract.

Figure 4:
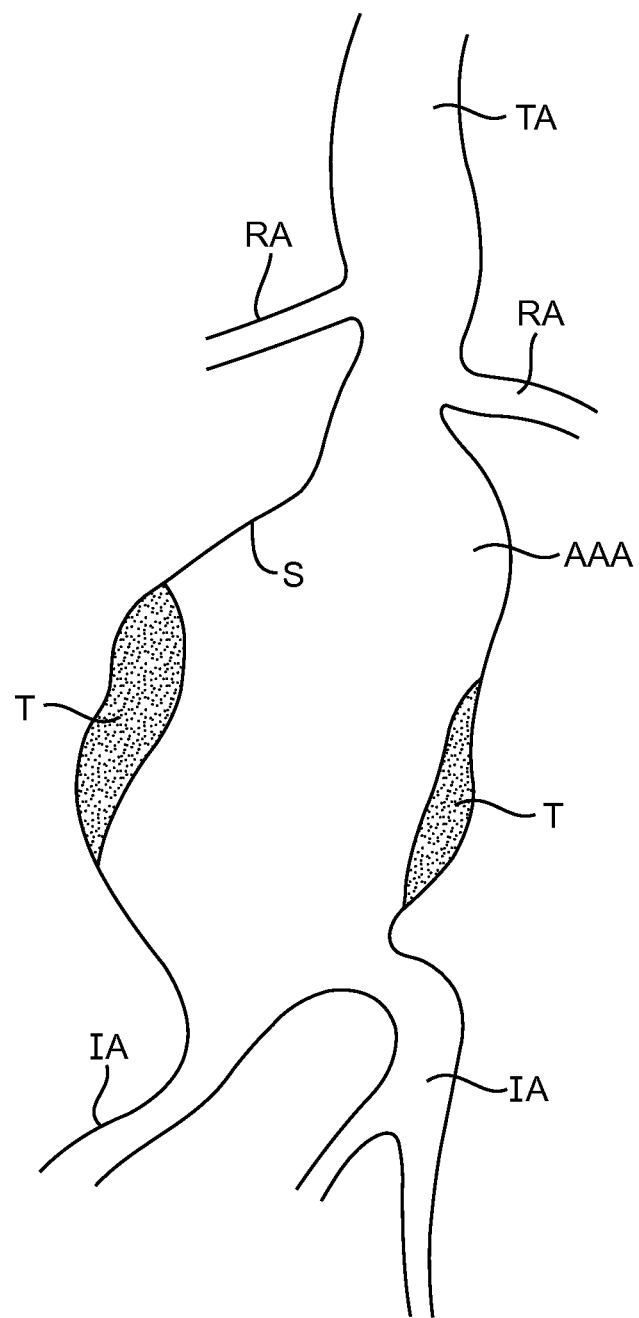
FIG. 4 illustrates the anatomy of an infrarenal abdominal aortic aneurysm.

Referring now to FIG. 4, the anatomy of an infrarenal abdominal aortic aneurysm comprises the thoracic aorta (TA) having renal arteries (RA) at its distal end above the iliac arteries (IA). The abdominal aortic aneurysm (AAA) typically forms between the renal arteries (RA) and the iliac arteries (IA) and may have regions of mural thrombus (T) over portions of its inner surface (S).

Figure 5A:
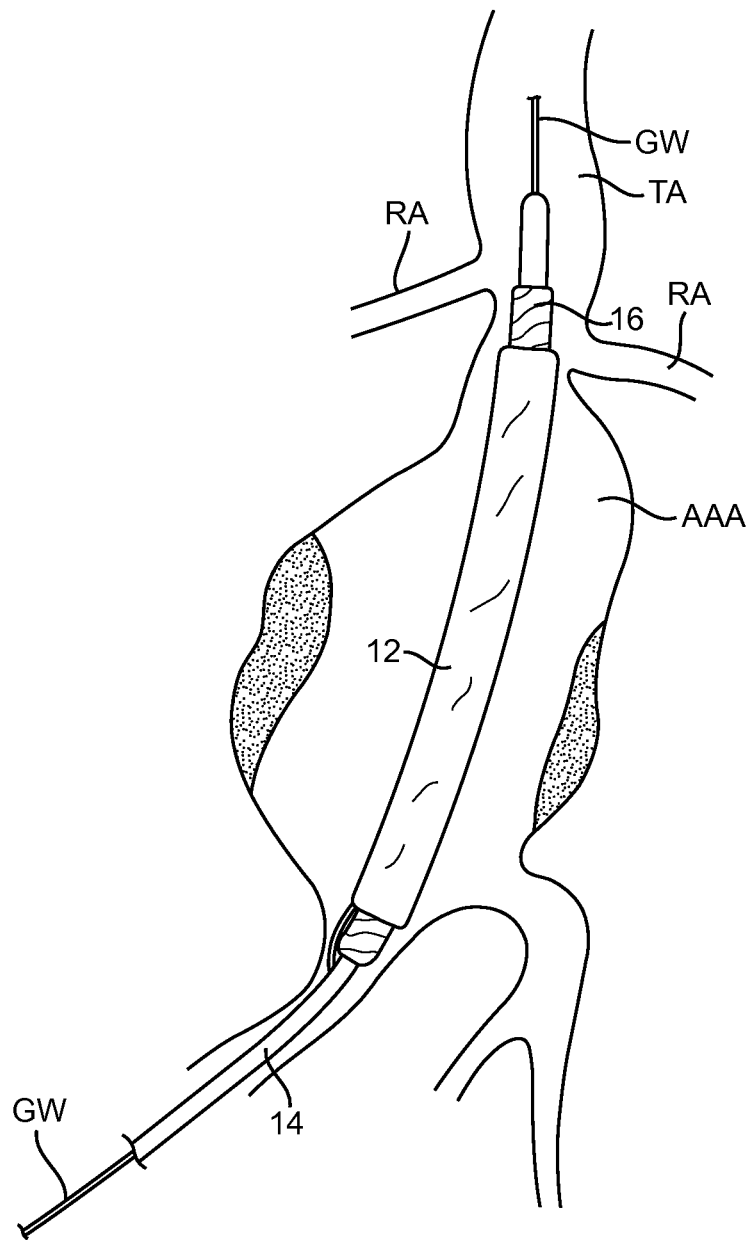
FIGS. 5A-5D illustrate use of the prosthesis system of FIG. 1 for treating an infrarenal abdominal aortic aneurysm.

Referring to FIGS. 5A-5D, the treatment system 10 of FIG. 1 may be utilized to treat the complex geometry of the transmural abdominal aortic aneurysm (AAA) of FIG. 4 by first positioning the delivery catheter 14 to place the double-walled filling structure 12 (in its unfilled configuration) generally across the aneurysm from the region of the aorta beneath the renal arteries (RA) to a region over the iliac arteries (IA), as best seen FIG. 5A. Usually, the delivery catheter 14 will be introduced over a guidewire (GW) through a puncture in the patient's groin accessing the iliac artery by the Seldinger technique.

After the double-walled filling structure 12 is properly positioned, a hardenable fluid filling medium 30 is introduced into the internal space 22 filling the inner space. Filling of the inner space 22 expands the outer wall 24 of the structure outwardly so that it conforms to the inner surface (S) of the aneurismal space. The filling structure may be oversized to allow for later expansion of the structure to accommodate changes in the size or volume of the aneurismal space over time. For example, the outer wall 24 of the structure may comprise folds or wrinkles so that when additional fluid, such as water vapor, enters the internal space 22 over time, the internal space 22 expands the outer wall 24 against the inner surface (S) of the aneurismal space unfurling the folds or wrinkles in the outer wall 24.

Figure 5B:
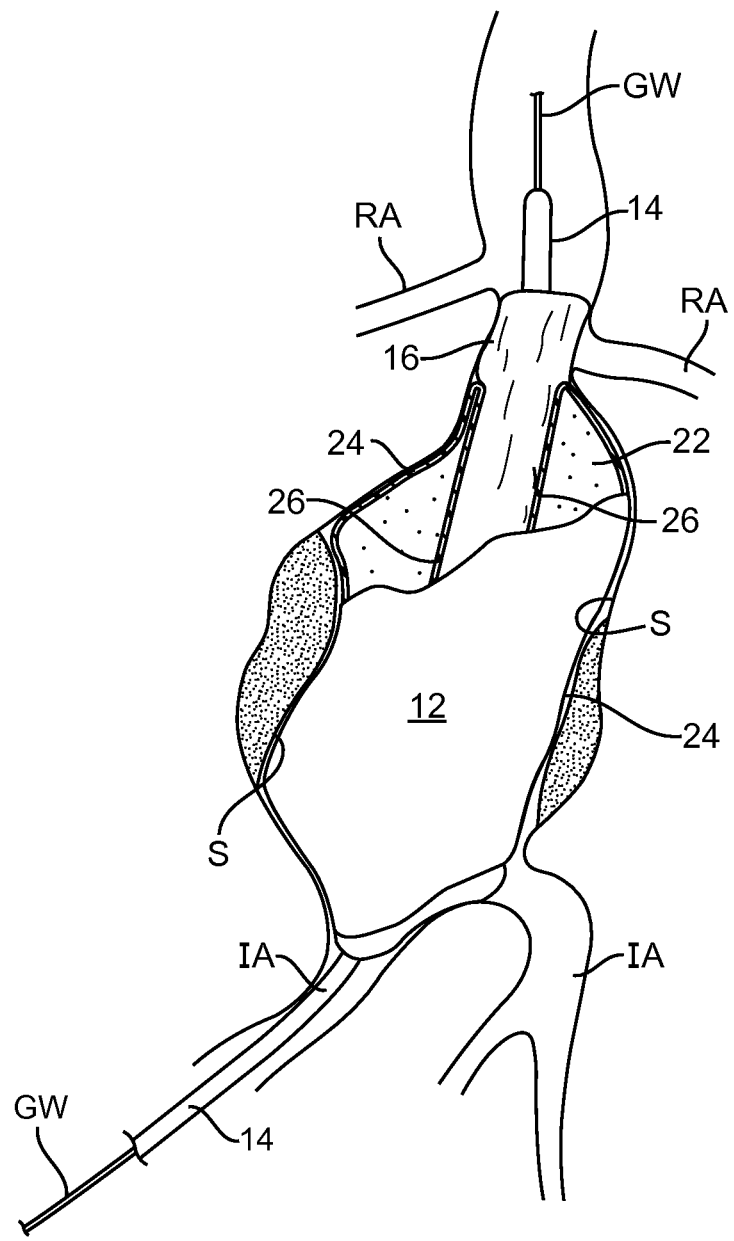

Before, during, or after filling of the double-walled filling structure 12 with inflation medium, or during combinations thereof, as illustrated in FIG. 5B, the balloon 16 or other expansible structure will also be inflated or expanded to open the tubular lumen defined by the interior of the inner wall 26. In a preferred embodiment, the balloon 16 will be generally compliant, typically having a maximum diameter or width which is at or slightly larger than the desired tubular lumen diameter or width through the deployed filling structure 12. The filling structure 12, in contrast, may be partially or completely formed from a generally non-compliant material, thus allowing the non-compliant balloon or other expansible structure 16 to fully open the tubular lumen and conform the ends of the lumens to the aorta and iliac walls, as illustrated in FIG.

5C. The filling structure 12 may also be partially or completely formed from a semi-permeable material, so as to allow diffusion of water molecules through the material in order to expand or shrink the filling structure. A lower or proximal end 50 of the tubular lumen will be flared to a larger diameter so that it can accommodate the openings into both of the iliac arteries (IA) as illustrated. Thus, it will be preferred to utilize a filling structure 12 geometry which has been chosen or fabricated to match the particular patient geometry being treated. It will also be preferable to use a balloon 16 or other expansible structure which will be shaped to preferentially open the lower proximal end 50 of the tubular lumen to a larger diameter than the upper or distal end 52. It may also be appreciated that a stent or scaffold may be placed in the generally tubular lumen before, during, or after deployment of the filling structure. Placement of the scaffold in the generally tubular lumen may allow for flow of blood through the lumen before, during, or after filling of the structure.

In another variation of the method, an optional contrast pre-filling step may be utilized. In this embodiment, after the delivery catheter is positioned across the aneurysm and the endoframe has been radially expanded, the filling structure may be pre-filled with contrast media and/or saline, or other fluids so as to permit observation of the filled filling structure under a fluoroscope relative to the aneurismal sac. Additionally, the pre-filling step allows the physician to record the pressure and volume of the contrast media used for optimal filling of the filling structure and this will provide an estimate of volume and pressure to be used when filling the filling structure with the hardenable filling material. In order to prevent overfilling of the filling structure, any of the pressure relief valves disclosed below may also be used to bleed off excess fluid from the filling structure.

After the filling material 30 has been introduced to the filling structure 12, typically through the filling tube 20, the fluid filling material 30 may be cured or otherwise hardened to provide for the permanent implant having a generally fixed structure which will remain in place in the particular aneurismal geometry. The filling material 30 is selected to have dissolvable solutes suitable for causing a desired osmolarity inside the filling structure, the desired osmolarity creating an osmotic pressure that causes a transfer of water molecules across the membrane resulting in expansion or shrinkage of the filling structure over time. The filling material 30 may also include a material having a variable osmolarity, such as an osmolarity that changes due to a filling material that releases solutes over time (e.g. a timed release). Methods for curing or hardening the filling material will depend on the nature of the filling material. For example, certain polymers may be cured by the application of energy, such as heat energy or ultraviolet light. Other polymers may be cured when exposed to body temperature, oxygen, or other conditions which cause polymerization of the fluid filling material. Still others may be mixed immediately prior to use and simply cure after a fixed time, typically minutes.

The filling structure may also include a scaffold placed into the tubular lumen defined by the inner wall 26, as illustrated in FIGS. 5D-5H. The scaffold may be a short, radially expandable structure, as in FIG. 5D, which may be implanted in the upper proximal opening 52 of the tubular lumen of the filling structure 12 in order to help anchor the upper end of the structure and prevent intrusion of blood into the region between the outer wall 24 and the inner surface S of the aneurysm and to generally improve the transition from the aorta into the tubular lumen. The radially expandable structure 60 may comprise any conventional stent, graft, or other expandable luminal support structure known in the arts. An alternative radially expandable structure 64 may span the entire length from the aortic end of the filling structure 12 to the iliac end, as in FIG. 5E. Radially expandable structure 64 could also comprise any conventional scaffold or graft structure, typically being an expandable metal frame optionally covered with a membrane to form a graft. A further alternative radially expandable structure 66 may extend fully through the filling structure and into the thoracic aorta TA, often covering the renal arteries RA, as in FIG. 5F. The portion of the radially expandable structure 66 which extends through the filling structure 12 will often be covered with a membrane or other protective material so that the structure is actually a graft within the filling structure. A portion of structure within the thoracic aorta TA, however, will preferably be left open to permit blood flow into the renal arteries RA.

Figure 5C:
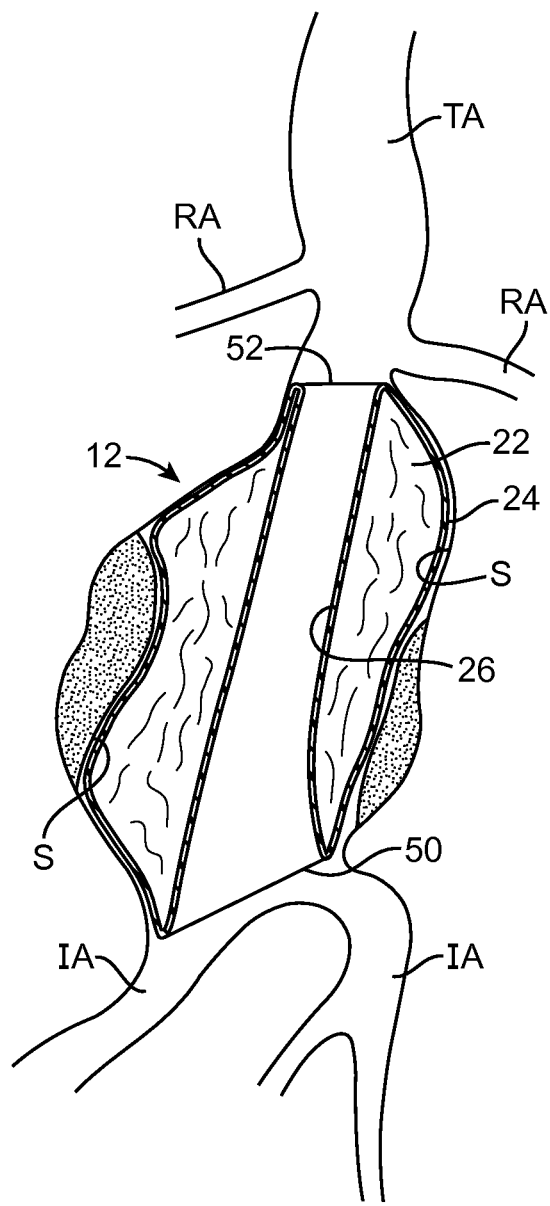
Figure 5D:
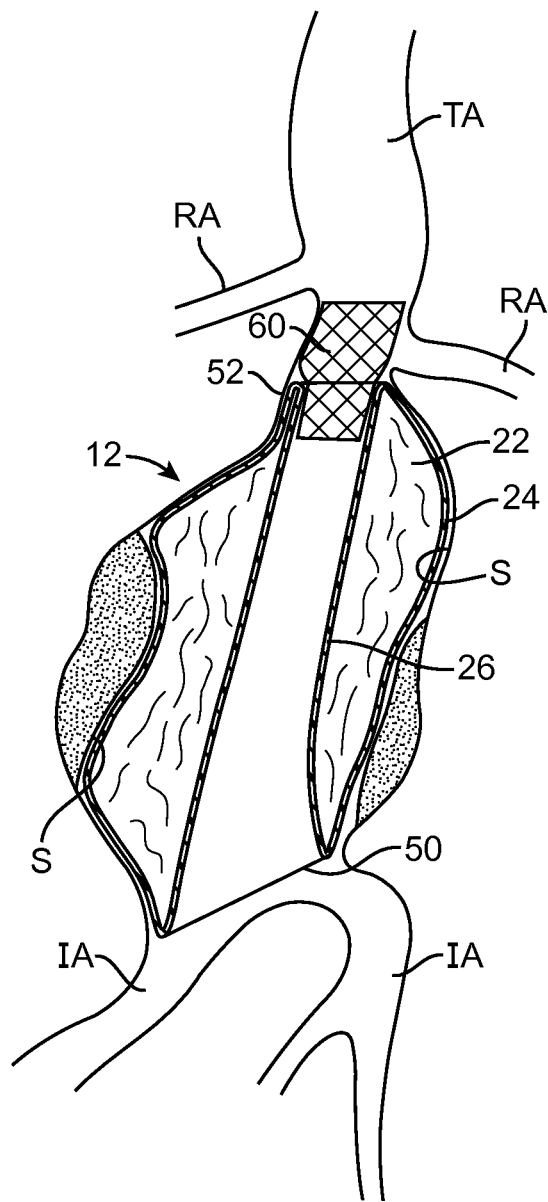
Figure 5E:
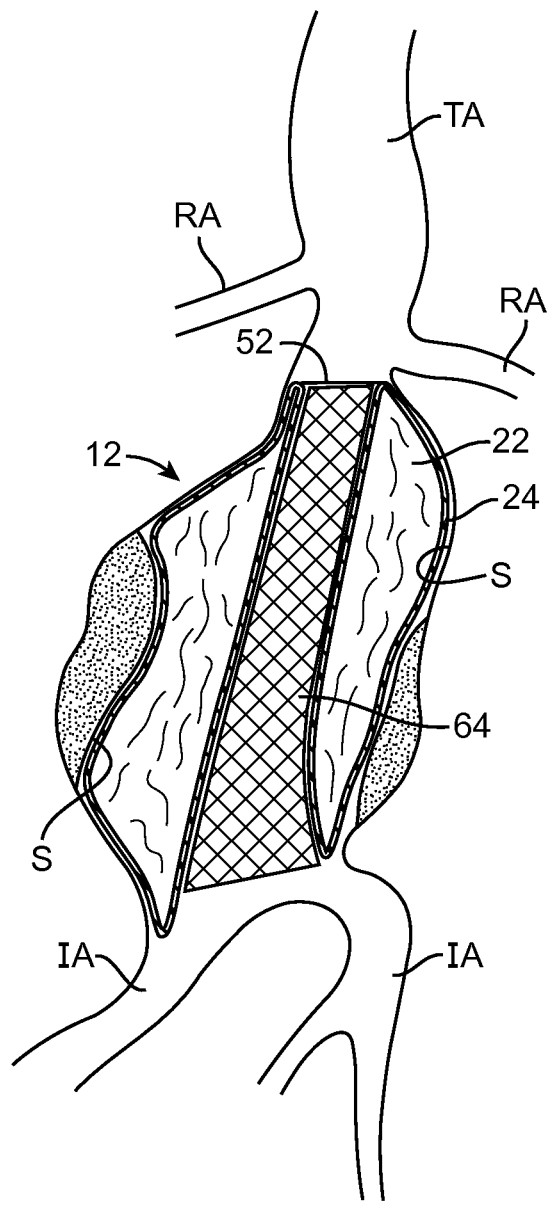
FIGS. 5E-5G illustrate the introduction of scaffolds into the tubular lumens of the filling structures of the systems of FIGS. 5A-5D.
Figure 5F:
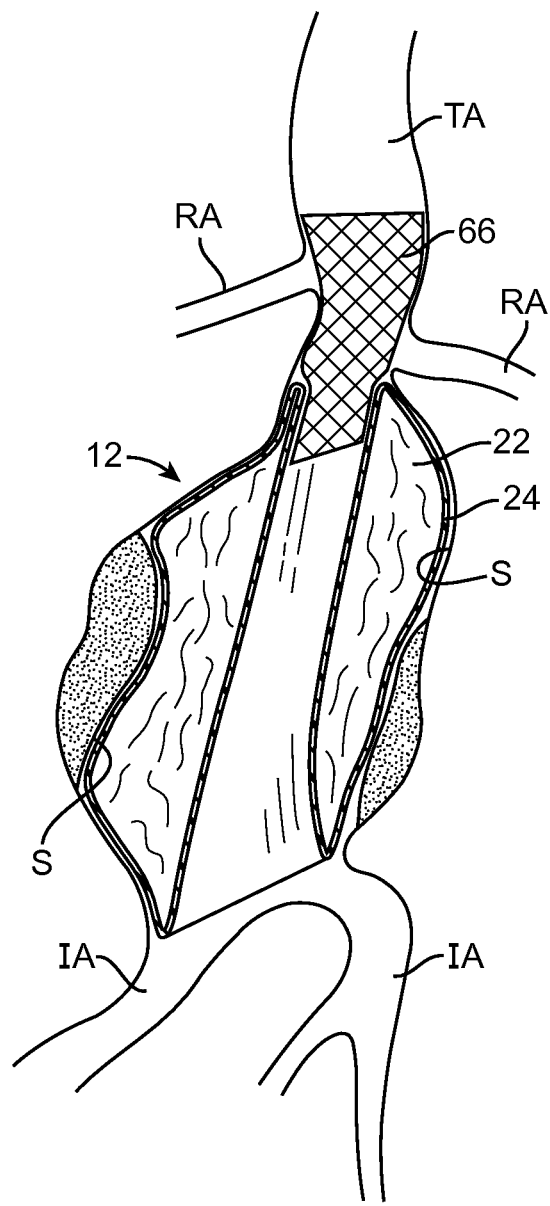
Figure 5G:
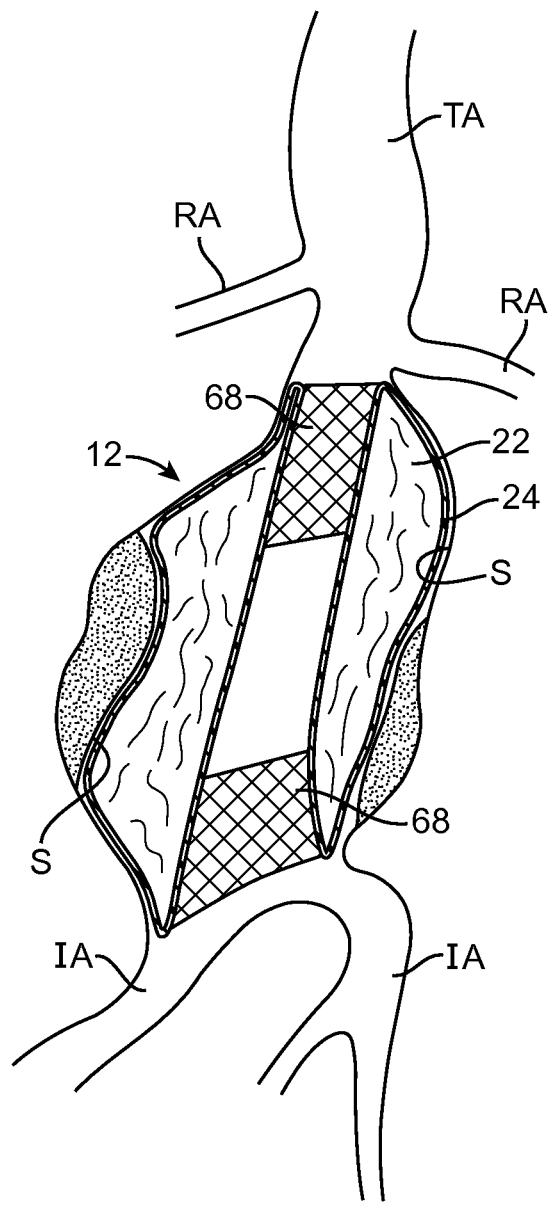

As shown in FIG. 5G, two or more radially expandable structures 68 may be implanted within the tubular lumen of the filling structure 12, as in FIG. 5G. As illustrated, the relatively short radially expandable structures 68 are positioned at the aortic side and the iliac side of the filling structure. They could be positioned elsewhere, and the segments could be longer and extend into either the aorta either or both of the iliacs. In another embodiment, two or more radially expandable structures 70 may be deployed within the tubular lumen of the filling structure 12 in an overlapping manner. By overlapping the segments (radially expandable structures) 70, the overall length of the structure can be adjusted, e.g., to fully cover the renal arteries if that is desired, or in other instances to avoid covering the renal arteries if that is what is desired.

The radially expandable structures, grafts, and other scaffold structures will often be delivered using separate delivery catheters (not shown) of the type commonly used to intravascularly deliver stents and grafts. The scaffold delivery catheters may comprise balloons or other expansion elements for expanding malleable scaffolds in situ. Alternatively, the delivery catheters could comprise tubular sheaths for covering and constraining self-expanding scaffolds prior to release within the tubular lumens of the filling structures. Systems could also deliver the scaffold(s) simultaneously with the filling structure(s), often on a common delivery catheter system.

Figure 6:
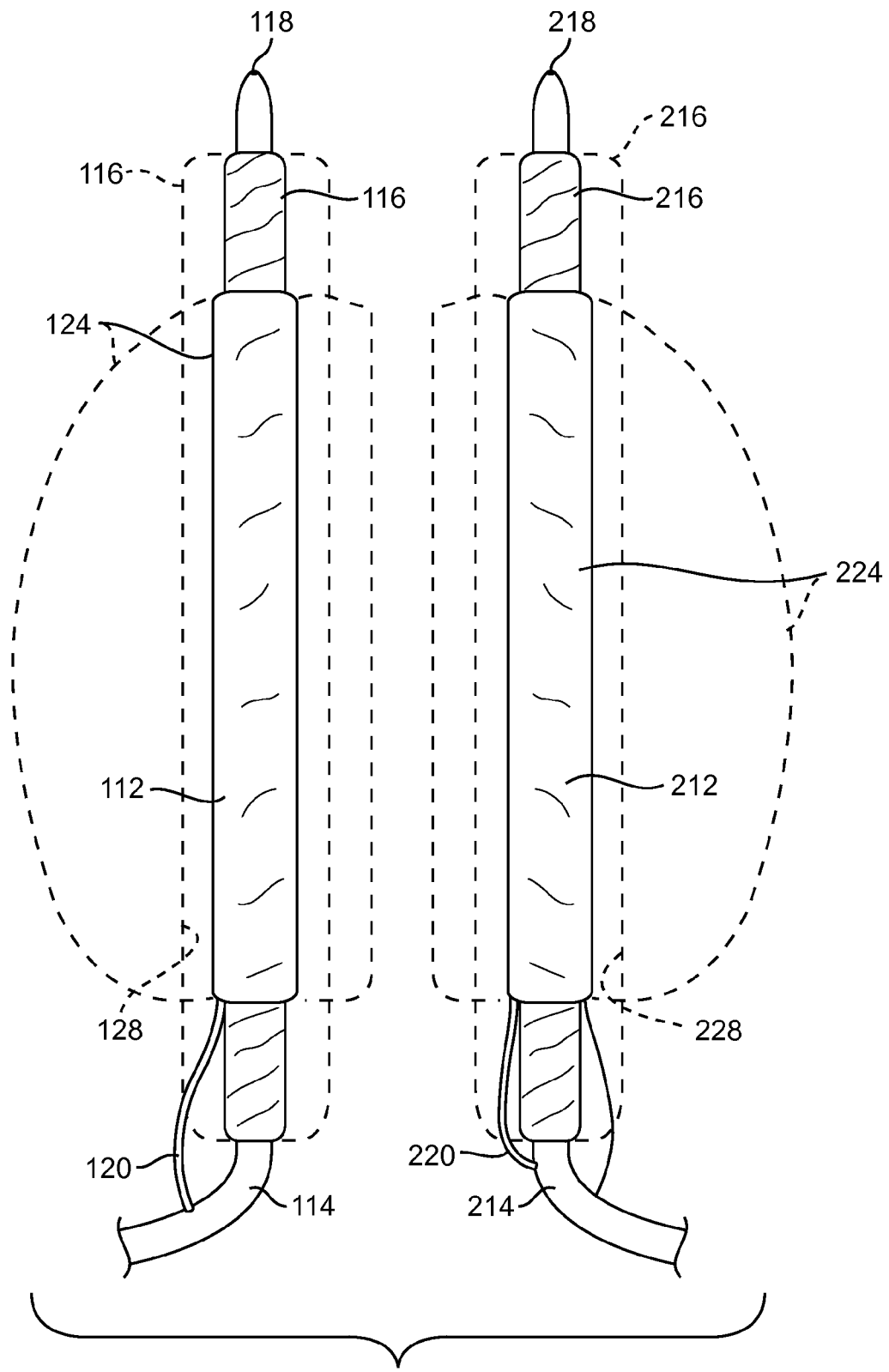
FIG. 6 illustrates a system comprising a pair of prostheses for delivery to an infrarenal abdominal aortic aneurysm, where each prosthesis comprises a filling structure mounted on a delivery catheter.

In another embodiment, a pair of double-walled filling structures will be used to treat infrarenal abdominal aortic aneurysms, instead of only a single filling structure as illustrated in FIGS. 5A-5C. A system comprising such a pair of filling structures is illustrated in FIG. 6 which includes a first filling structure 112 and a second filling structure 212. Each of the filling structures 112 and 212 are mounted on delivery catheters 114 and 214, respectively. The components of the filling structures 112 and 212 and delivery catheters 114 and 214 are generally the same as those described previously with respect to the single filling structure system 10 of FIG. 1. Corresponding parts of each of the fillings structures 112 and 212 will be given identical numbers with either the 100 base number or 200 base number. A principal difference between the filling structures 112 and 212, on the one hand, and the filling structure 12 of FIG. 1 is that the pair of filling structures will generally have asymmetric configurations which are meant to be positioned adjacent to each other within the aneurismal space and to in combination fill that space, as will be described with specific reference to FIG. 7A-7F below.

Figure 7A:
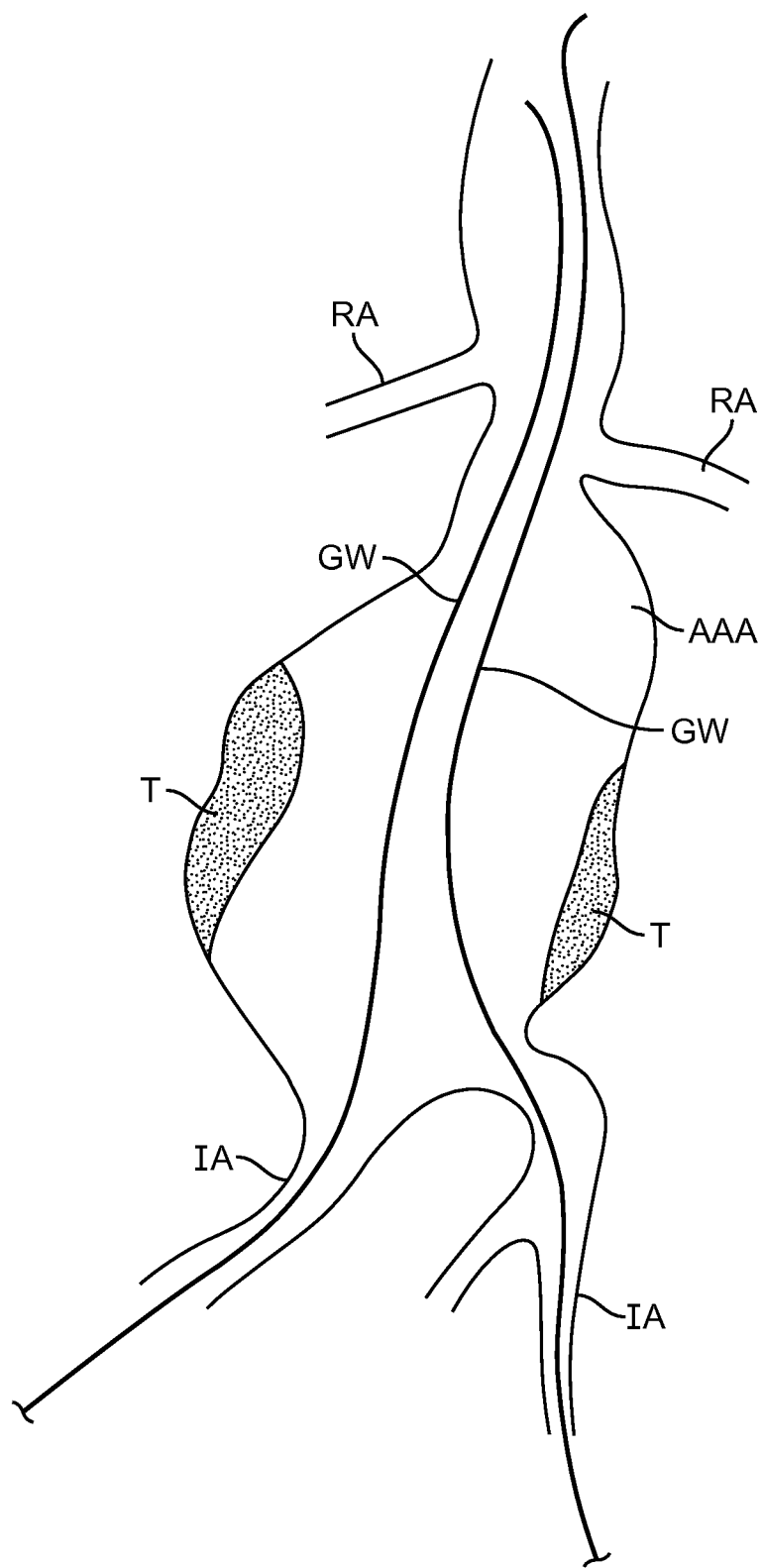
FIGS. 7A-7G illustrate use of multiple filling structures of the prosthesis system of FIG. 6 for treating an infrarenal abdominal aortic aneurysm.
Figure 7B:
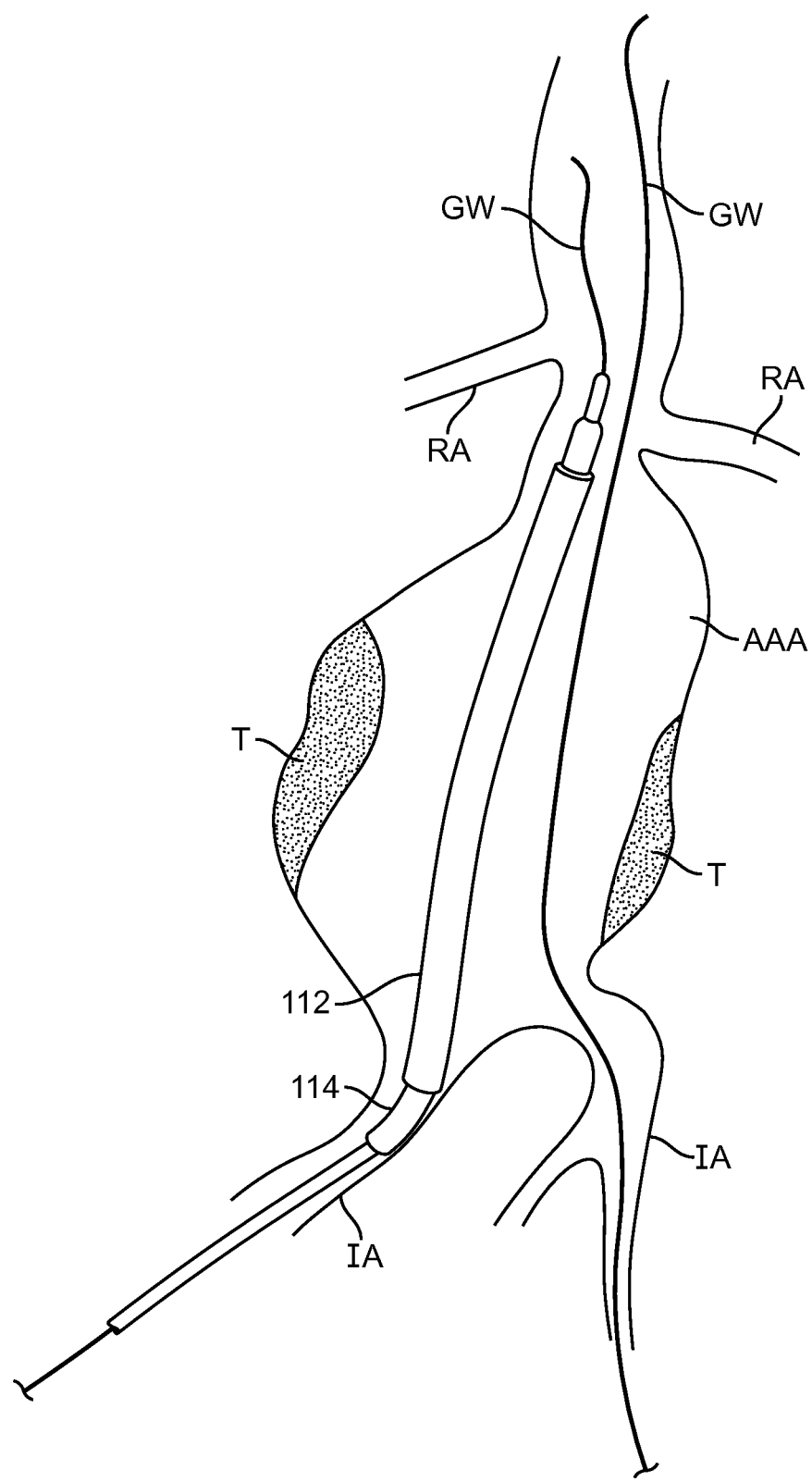
Figure 7C:
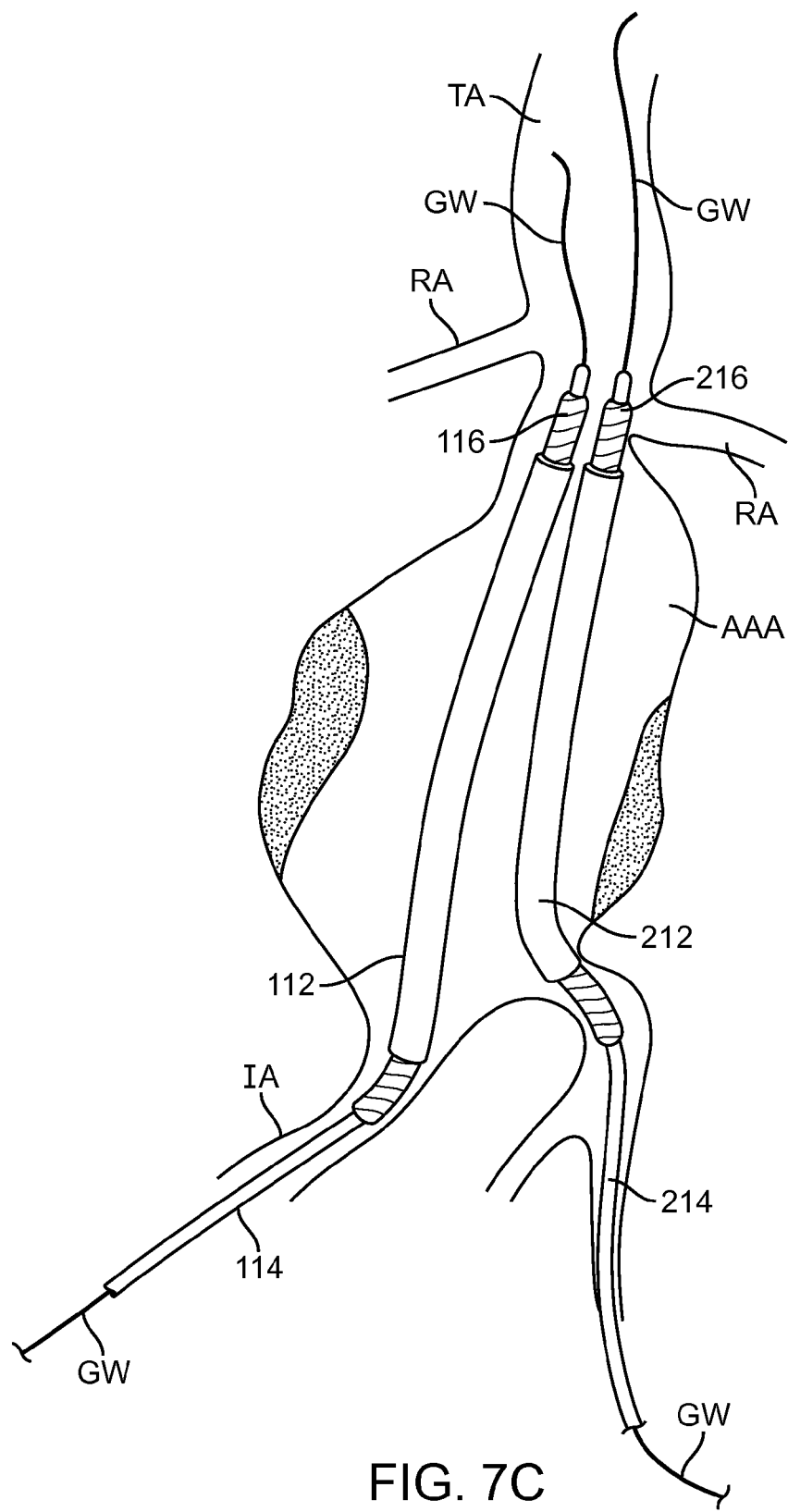
Figure 7D:
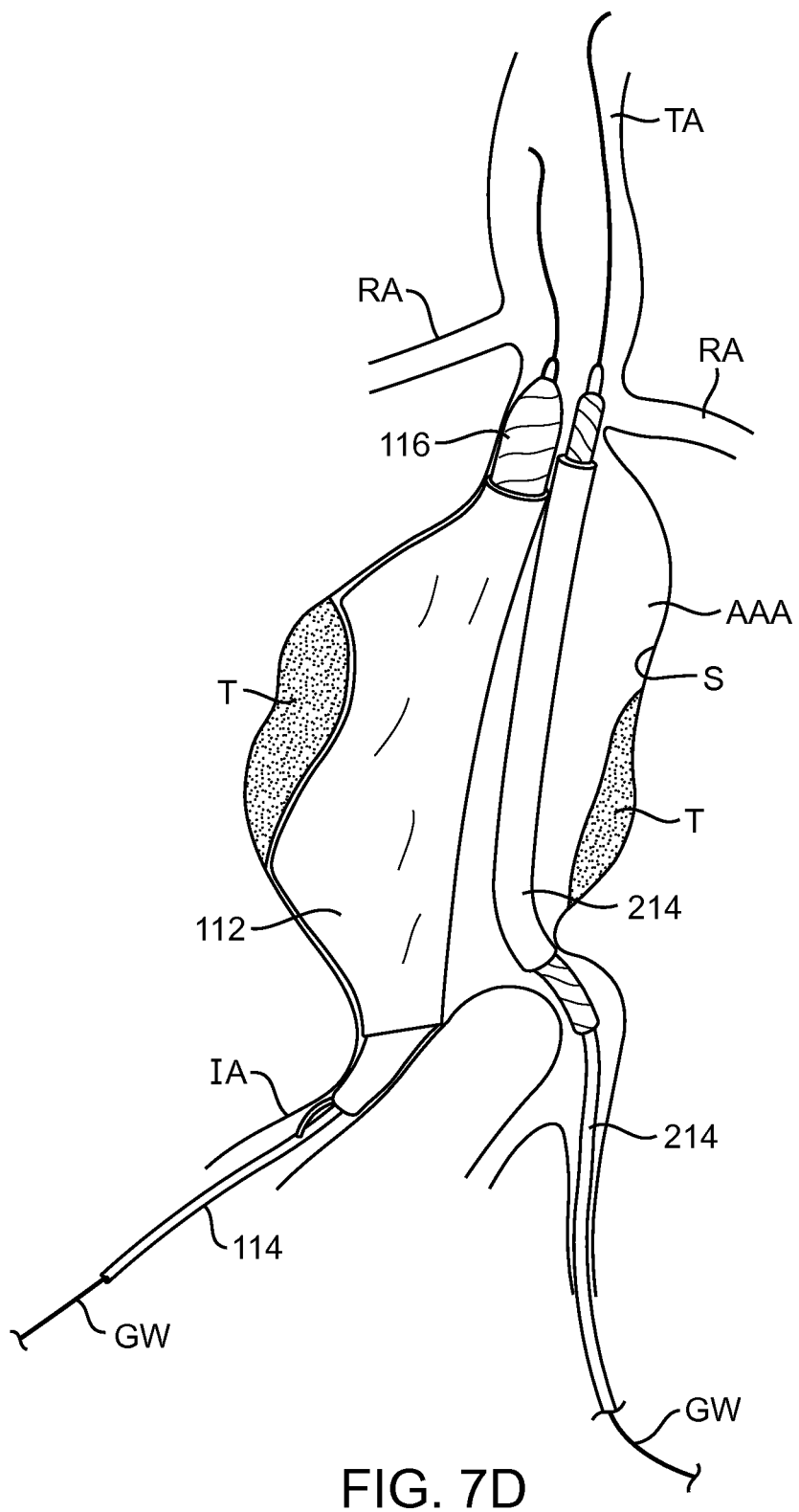
Figure 7E:
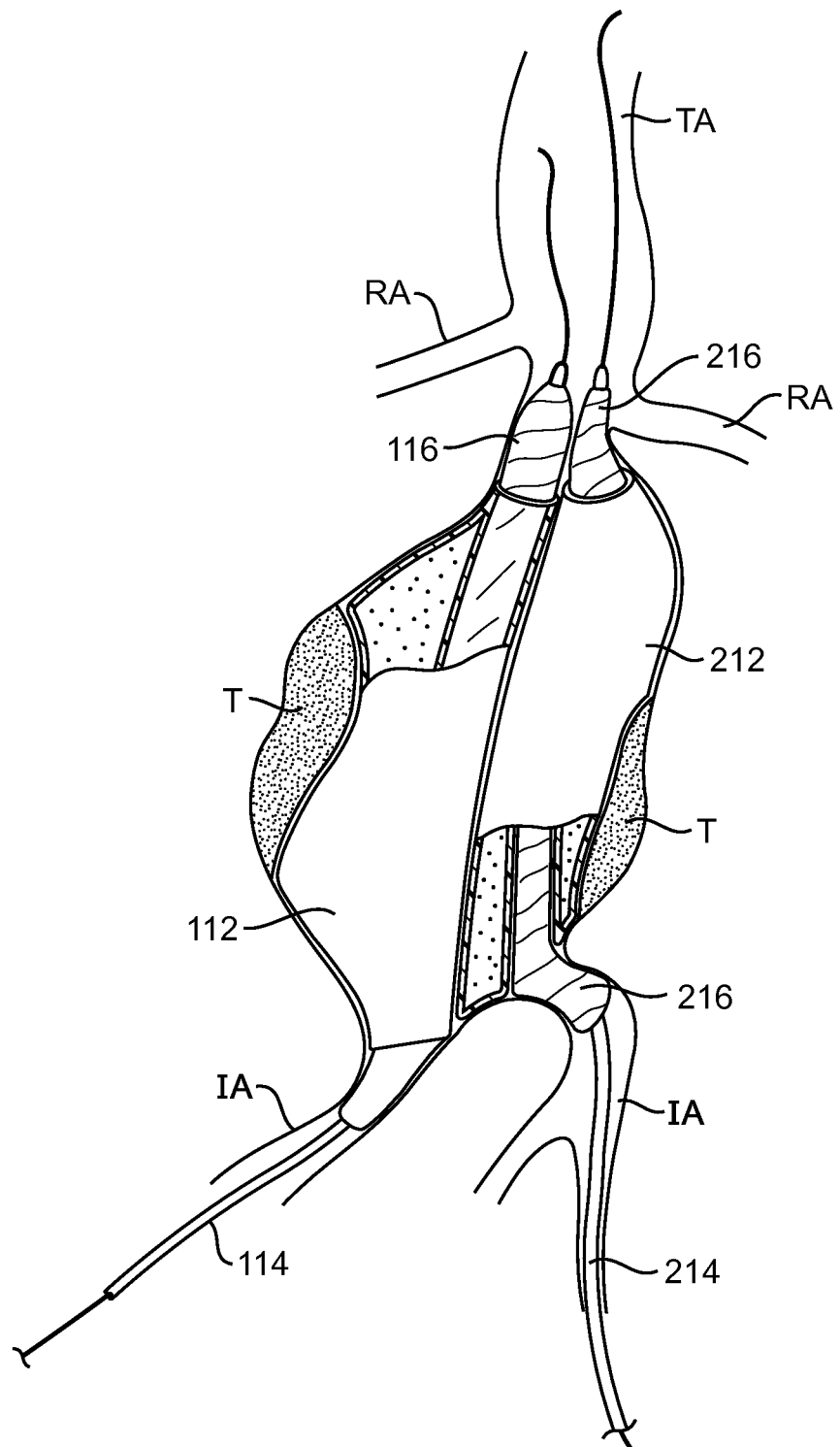

In treating an infrarenal abdominal aortic aneurysm using the pair of filling structures 112 and 212 illustrated in FIG. 6, a pair of guidewires (GW) will first be introduced, one from each of the iliac arteries (IA), as illustrated in FIG. 7A. The first delivery catheter 114 will then be positioned over one of the guidewires to position the double-walled filling structure 112 across the aortic aneurysm (AAA), as illustrated in FIG. 7B. The second delivery catheter 214 is then delivered over the other guidewire (GW) to position the second filling structure 212 adjacent to the first structure 112 within the aneurysm (AAA), as illustrated in FIG. 7C. Typically, one of the filling structures and associated balloons will be expanded first, followed by the other of the filling structures and balloon, as illustrated in FIG. 7D where the filling structure 112 and balloon 116 are inflated to fill generally half of the aneurismal volume. Filling can generally be carried out as described above with the one filling structure embodiment, except of course that the filling structure 112 will be expanded to occupy only about one-half of the aneurismal volume. After the first filling structure 112 has been filled, the second filling structure 212 may be filled, as illustrated in FIG. 7E. In other protocols the two filling structures may be filled simultaneously. The upper ends of the balloons 116 and 216 will conform the tubular lumens of the filling structures against the walls of the aorta as well as against each other, while the lower ends of the balloons 116 and 216 will conform the tubular lumens into the respective iliac artery (IA).

Figure 7F:
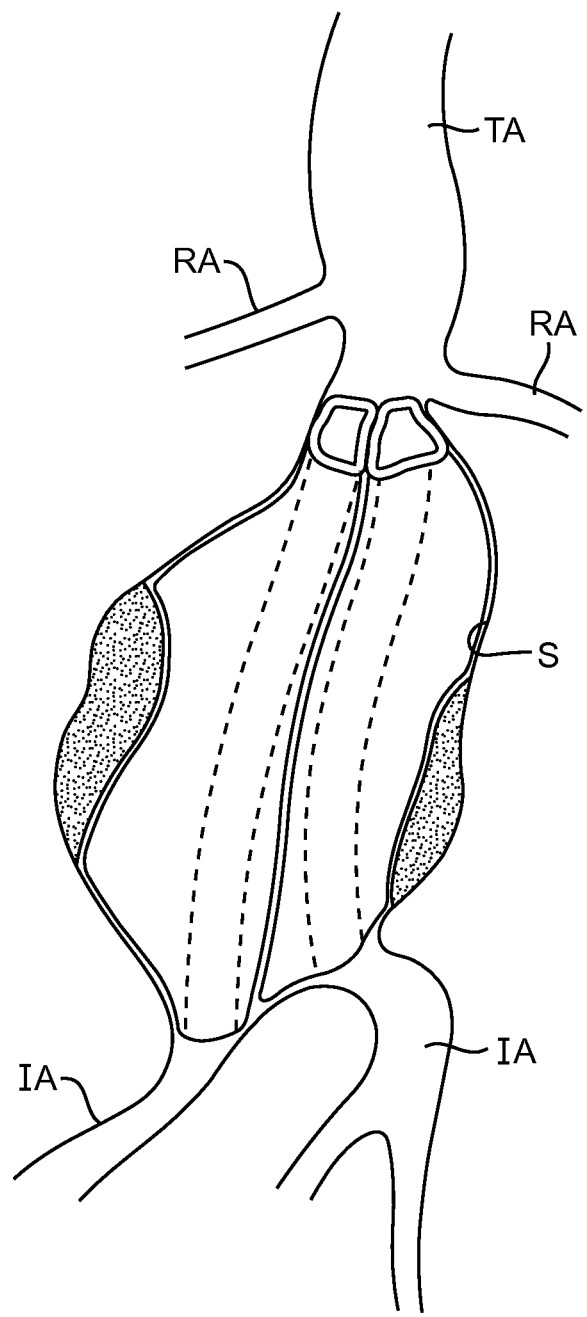

After filling the filling structures 112 and 212 as illustrated in FIG. 7E, the filling materials or medium will be cured or otherwise hardened, and the delivery catheters 114 and 214 removed, respectively. The hardened filling structures will then provide a pair of tubular lumens opening from the aorta beneath the renal arteries to the right and left iliac arteries, as shown in broken line in FIG. 7F. The ability of the filling structures 112 and 212 to conform to the inner surface (S) of the aneurysm, as shown in FIG. 7F, helps the structures to remain immobilized within the aneurysm with little or no migration. Immobilization of the filling structures 112 and 114 may be further enhanced by providing any of the surface features described above in connection with the embodiments of FIG. 2.

As with the single filling structure embodiments described previously, the double filling structure embodiments may include at least one separate scaffold deployed within each of the tubular blood flow lumens. The scaffolds will generally be radially expandable structures or graft-like vascular structures and will be deployed within the tubular lumens using balloon or other expansion catheters (in the case of malleable or balloon-expandable scaffolds) or using constraining sheaths (in the case of self-expanding scaffolds). The filling structures of the double filling structure embodiments may be positioned substantially parallel to each other, placed side-by-side so as to allow blood flow into right and left iliac arteries. The scaffolds may also be positioned substantially parallel to one another, placed side-by-side within each of the filling structures of the double filling structure embodiment. One of skill in the art would appreciate that while filling structures in such embodiments may be substantially parallel in the coronal plane, with the structures may form a cross (X-shape) in the sagittal plane, or that the structure may be substantially parallel in the sagittal plane, with the structures forming a cross (X-shape) in the coronal plane.

Figure 7G:
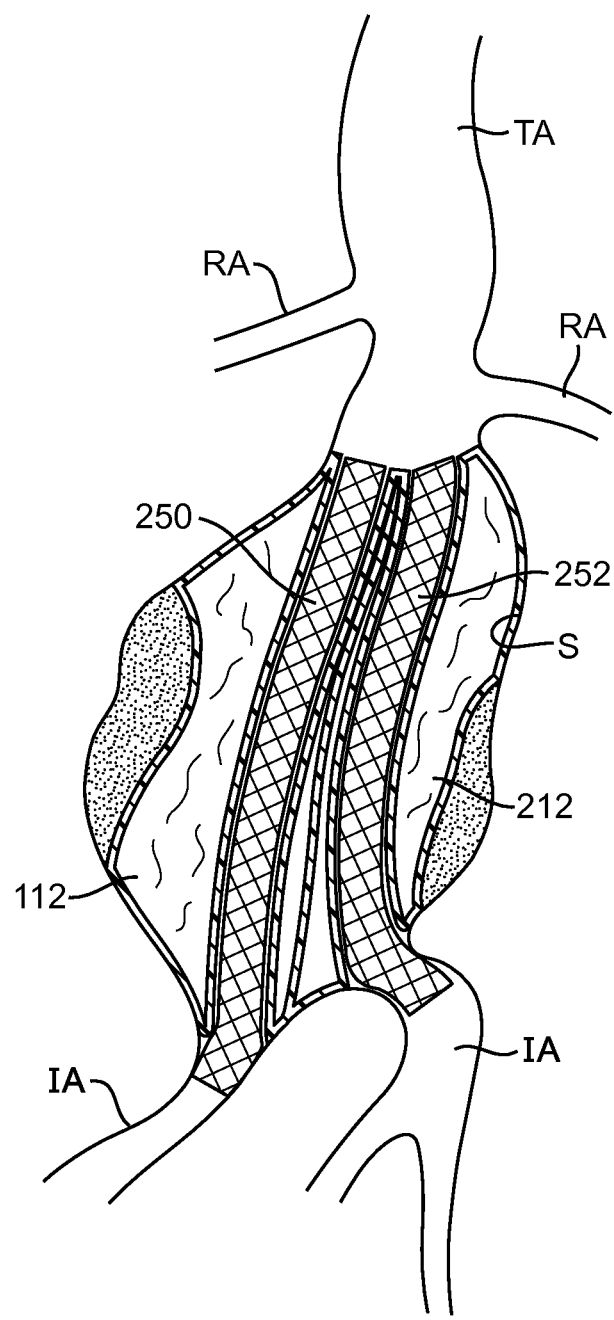

Referring in particular to FIG. 7G, the first scaffold 250 may be placed in the tubular lumen of the first filling structure 112 while a second scaffold 252 may be placed in the tubular lumen of the second filling structure 212. As illustrated, the scaffolds are stent-like structures which extend into the iliac arteries IA at the lower end of the filling structures.

Referring now to FIGS. 8A and 8B, the filling structure may comprise one or more semi-permeable bags 80 that expand to accommodate inflow of fluid in order to maintain apposition between the filing structure and the aneurysm. The multiple bags may comprise discrete independent bags or one bag having multiple compartments. As shown in FIGS. 8A-8B, the filling structure includes multiple semi-permeable bags that can be filled with a fluid filling medium, such as PEG, and which can further expand to accumulate fluid, such as water molecules. The use of separate mini-oversized bags may allow the filling structure to accommodate localized changes in the thrombus and help prevent uncontrolled expansion of the filling structure by limiting movement of fluid within the filling structure. In this embodiment, the multiple bags may be used in combination with an endoframe covered with an impermeable membrane sleeve thereby eliminating fluid transfer from the blood lumen of the filling structure in to the aneurysm sac. In a preferred embodiment, the semi-permeable bags 80 incorporate water molecules transported directly from the resolving thrombus post treatment, while the impermeable covered endoframe prevents fluid transfer from blood. FIG. 8A depicts the filling structure at the time of initial treatment (t=0), the outer wall in apposition with the thrombus of the aneurysm. FIG. 8B depicts the filling structure at a later time (t=n, n>0) after which the thrombus has resolved increasing the inner volume of the aneurysm. In FIG. 8B, the multiple semi-permeable bags have absorbed water molecules from the serum of the thrombus, thereby expanding against the thrombus to remain in apposition with inside surface S.

Referring now to FIGS. 9A and 9B, the filling structure may include a mesh disposed inside the inner volume of the filling structure. The mesh 90 is comprised of wires or threads made from polymer, wire, or any material sufficient to interlock with the fillable medium so as to secure the fillable medium within the fillable structure preventing unwanted movement of the medium within the inner volume. A fillable medium, such as a polymer hydrogel, is injected into the filling structure 12 and flows around mesh 90 and then cures. The mesh wires become physically interlocked with the hydrogel cast around it, thereby securing the polymer hydrogel to the inner wall of the filling structure. The mesh contributes towards keeping the filling medium secured in place, helps control the expansion of the bag, and helps control movement of the filling structure with reference to the tillable medium. For example, as illustrated, the mesh emanates from the inner wall which defines the blood lumen through the filling structure. As the polymer hydrogel is secured to the inner wall, the cured hydrogel secures the size and shape of the inner wall and associated blood lumen, while allowing the outer wall of the filling structure to expand and accommodate changes in the thrombus on the inside of the aneurysm. FIG. 9A depicts the mesh before filling with the tillable medium, while FIG. 9B depicts the mesh 90 interlocked with the cured filling medium.

Figures 10A, 10B:
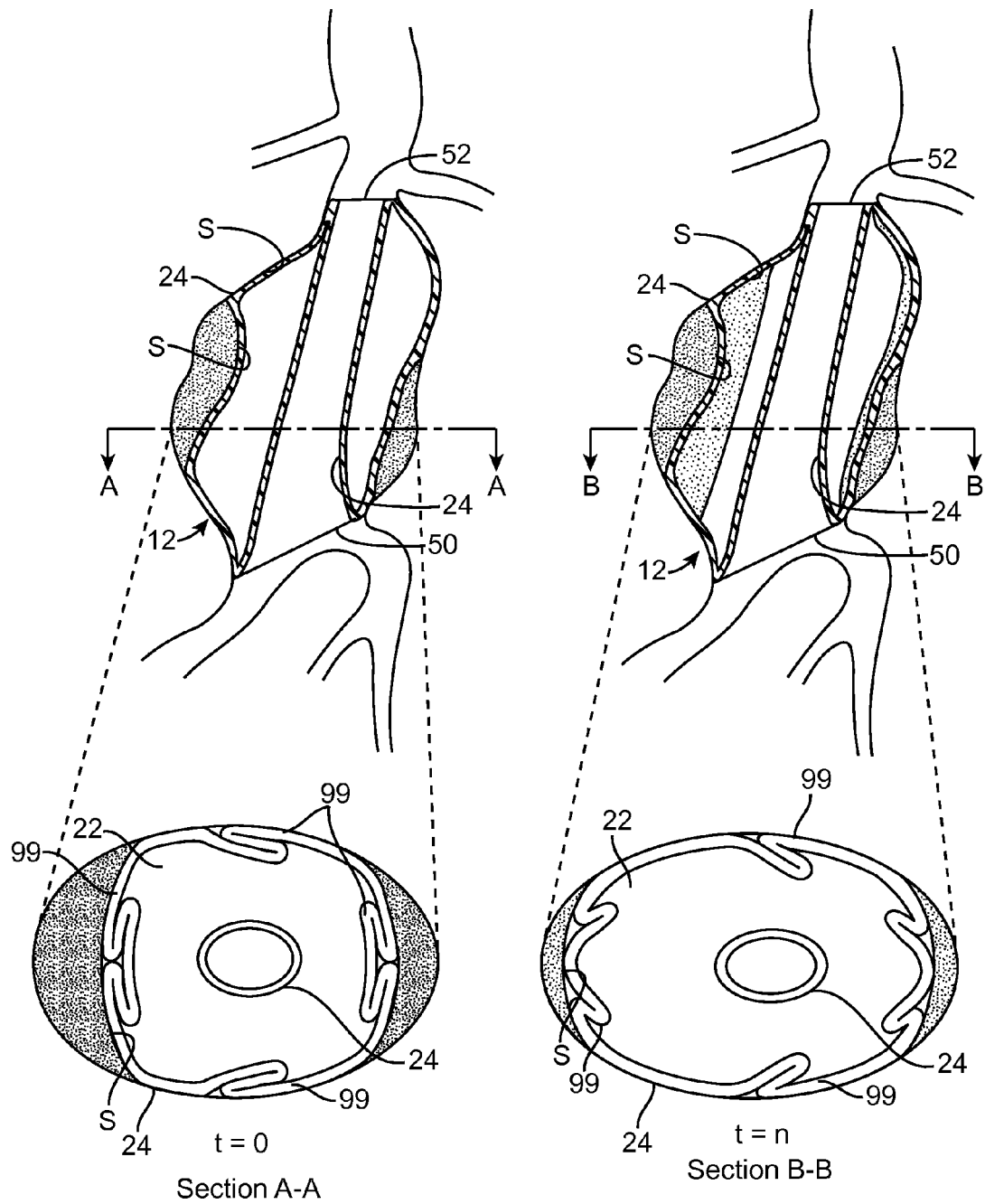
FIGS. 10A-10D illustrates a prosthesis system comprising a filling structure having folds in the outer wall to allow for expansion of the filling structure.
Figure 10C:
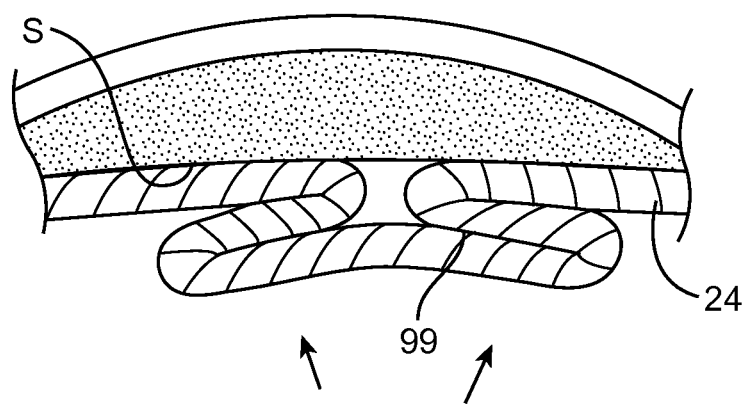
Figure 10D:
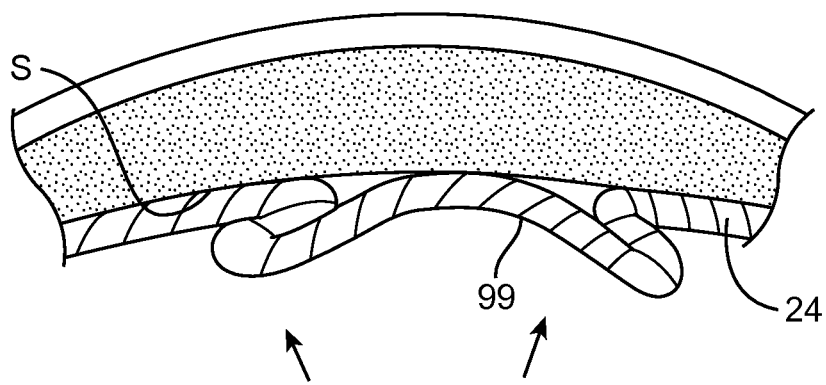

Referring now to FIGS. 10A-10D, the filling structure 12 may be oversized, meaning the capacity of the inner volume 22 may be greater than the initial filled volume when deployed in the aneurysm. The use of an oversized filling structure allows for expansion as the thrombus resolves. To ensure apposition at the initial time of deployment (t=0), the outer wall 24 of the filling structure 12 may include folds 99, also referred to as folds or wrinkles. As the thrombus resolves and the inner volume 22 of the filling structure increases due to inflow of water molecules (or in some embodiments serum), the outer wall 24 expands by unfurling the folds 99, thereby allowing the outer wall 24 of the filling structure to remain in apposition against the thrombus and/or inside surface S. FIG. 10A depicts the deployed filling structure at the time of initial treatment (t=0), in which the outer wall 24 is in apposition with the inside surface S of the aneurysm, the slack in the outer wall 24 of the oversized filling structure taken up within the folds 99. The pressure of the filling medium within the inner space 22 of the filling structure 12 press the outer wall 24 against the inside surface S. FIG. 10B depicts the filling structure at a later time (t=n, n>0) at which the thrombus has resolved, thereby increasing the inner volume of the aneurysm. As the thrombus resolves, the folds 99 of the outer wall unfurl as water molecules flow into the filling structure, thereby maintaining the seal against the aneurysm wall and maintaining apposition against the thrombus and inside surface (S) of the aneurysm. FIGS. 10C-10D provide a detail of a fold at 99 of the outer wall 24 as it unfurls or unfolds to accommodate changes in the inner volume of the aneurysm due to resolution of the thrombus.

Figure 11A:
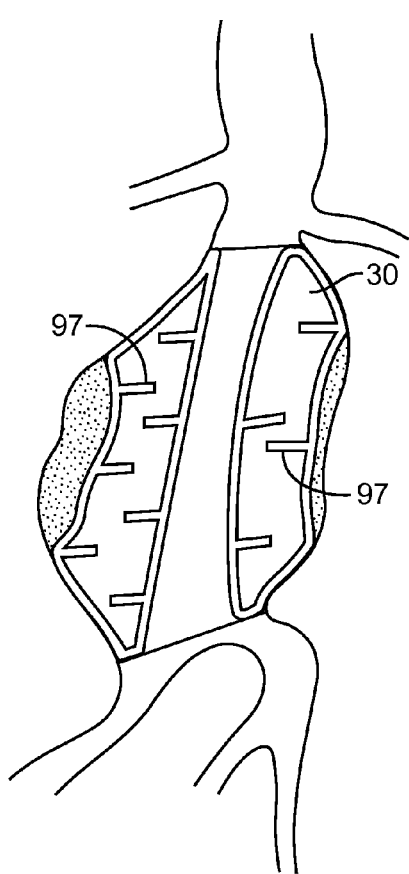
FIGS. 11A-11B illustrate embodiments having chambers.
Figure 11B:
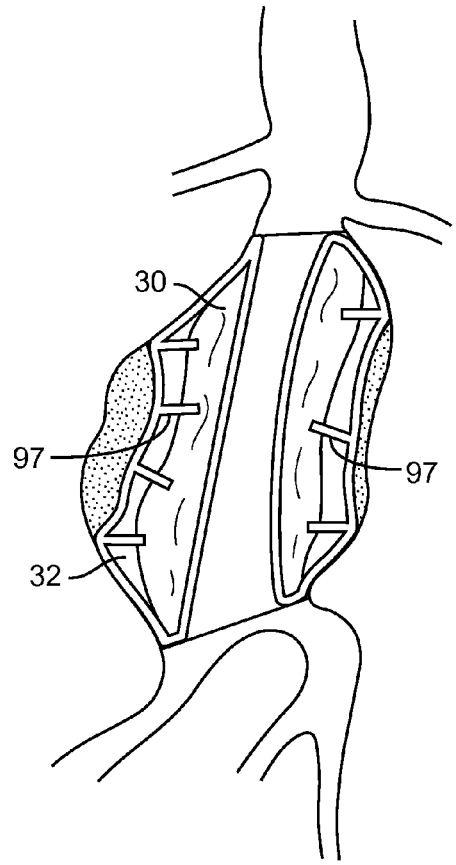

Various modifications of the protocols described above will be within the scope of the present invention. For example, while the inner space is often depicted as one large space, it would also be possible to design the inner space of the filling structure as multiple spaces, interconnected or separate, or to design the inner space to have chambers or baffled regions to control fluid flow and expansion or shrinkage of the filling structure. FIGS. 11A-11B depict embodiments including chambers 97 within the fillable space. The chambers 97 include baffles coupled to the inner or outer wall that protrude into the fillable space so as to control movement of the filling medium and/or control or limit movement of fluid flowing into or out from the filling structure over time. Additionally, while the osmolarity of fluid within the filling structure is often controlled through selection of the filling medium material, one of skill in the art would appreciate alternative ways in which to control the water potential, including controlling fluid pressure, expansion of the fluid filling medium, addition of solutes directly into the filling structure, or altering the ability of the semi-permeable material to diffuse water molecules and/or serum.

Additional information regarding various aspects of apparatus and methods for treatment generally related to the present application can be found in the following applications: U.S. application Ser. No. 08/620,072 now U.S. Pat. No. 5,665,117; U.S. application Ser. No. 12/478,225; U.S. application Ser. No. 12/478,208; U.S. application Ser. No. 12/371,087; U.S. application Ser. No. 12/429,474; U.S. application Ser. No. 11/752,750 now U.S. Pat. No. 7,790,273; U.S. application Ser. No. 11/444,603; U.S. application Ser. No. 11/413,460; U.S. application Ser. No. 12/684,074; U.S. application Ser. No. 11/482,503 now U.S. Pat. No. 7,666,220; U.S. application Ser. No. 12/421,297; U.S. application Ser. No. 11/187,471 now U.S. Pat. No. 7,530,988; U.S. application Ser. No. 11/876,458; U.S. application Ser. No. 10/668,901; and U.S. application Ser. No. 10/787,404, the full disclosures of which are incorporated herein by reference.

While the above provides a complete description of particular embodiments, various alternatives, modifications, and equivalents may be used. One of skill in the art would appreciate that various features of separate embodiments may be combined in accordance with the principles of the invention. Therefore, the above description should not be taken as limiting the scope which is defined by the appended claims.

What is claimed is:

1. A system for treating an aneurysm in a blood vessel, said system comprising:
at least a first double-walled filling structure comprising an outer wall, an inner wall, and a fillable space therebetween such that when filled, the outer wall conforms to the inside surface of the aneurysm and the inner wall forms a first generally tubular lumen to provide a path for blood flow, wherein the filling structure further comprises a membrane, the membrane permeable to water molecules so as to allow transport of water molecules across the membrane between the fillable space and an environment outside the filling structure when a water potential differential exists across the membrane; and
a fluid filling medium for filling said fillable space, the fluid filling medium having one or more dissolvable solutes,
wherein the membrane is impermeable to the one or more dissolvable solutes of the fluid filling medium such that the one or more dissolvable solutes induces an osmotic gradient across the membrane, and
wherein the outer wall of the first double-walled filling structure remains flexible after deployment within the aneurysm such that the filling structure accommodates changes in a size and shape of the aneurysm when the aneurysm changes shape after deployment.

2. The system according to claim 1, wherein the transport of water molecules across the membrane is caused by the osmotic gradient induced by a difference in osmolarity across the membrane.

3. The system according to claim 1, wherein the membrane comprises a semi-permeable material such that the osmotic gradient across the membrane causes water molecules to permeate across the membrane.

4. The system according to claim 1, further comprising: a scaffold placed within at least a portion of the generally tubular lumen.

5. The system according to claim 1, wherein the fluid filling medium comprises one or more fluid filling media that include a hardenable polymer.

6. The system according to claim 5, wherein the fluid filling medium comprises a hydrophilic polymer having the one or more dissolvable solutes in a concentration sufficient to induce a desired osmotic gradient across the membrane.

7. The system according to claim 5, wherein the fluid filling medium further comprises serum and/or transudate.

8. The system according to claim 5, wherein the fluid filling medium further comprises a hyperosmotic medium relative to human blood.

9. The system according to claim 5, wherein the hardenable polymer comprises an aqueous polyethylene glycol (PEG)-diacrylate based formulation comprising the one or more dissolvable solutes designed to maintain hypertonic and hyperosmotic conditions within the fillable space.

10. The system according to claim 5, further comprising:
a scaffold placed within at least a portion of the generally tubular lumen.

11. The system according to claim 1, wherein the outer and/or inner walls comprise ePTFE having an internodal distance ranging from 0.3 nanometers to 5 microns.

12. The system according to claim 1, wherein the fillable structure is configured such that, after deployment within the aneurysm, a flux rate of water through the membrane is between 0.01 to 0.03 mL/day/cm$^2$.

13. The system according to claim 1, wherein the filling structure has a total filling capacity that is greater than the aneurysmal space so as to allow for expansion of the filling structure to accommodate changes in a volume of the aneurysm.

14. The system according to claim 1, wherein the filling structure comprises one or more discrete semi-permeable bags that can separately expand when filled with fluid in response to transfer of fluid into the fillable space.

15. A self-adjusting endograft for treating an aneurysm in a blood vessel, said endograft comprising:
a generally tubular lumen to provide a path for blood flow body through the endograft;

a fillable component having a fillable space in fluid communication with an exterior environment surrounding the endograft across a semi-permeable membrane that is impermeable to one or more dissolvable solutes disposed within the fillable space;

wherein the semi-permeable membrane allows transfer of fluid into the fillable space when a water potential within the fillable space is less than a water potential of an environment directly outside the endograft, the water potential being associated with an osmotic gradient induced by the one or more dissolvable solutes within the fillable space;

wherein the semi-permeable membrane allows flow of fluid out from the fillable space when the water potential within the fillable space is greater than the water potential of an environment directly outside the endograft, the water potential being associated with the osmotic gradient induced by the one or more dissolvable solutes within the fillable space; and an outer wall adapted to conform to an inside surface of the aneurysm when the fillable space is filled and to remain flexible after deployment within the aneurysm such that transfer of fluid into and out from the fillable space conforms the outer wall to the inside surface of the aneurysm such that the filling structure accommodates changes in a size and shape of the aneurysm when the aneurysm changes shape after deployment.

16. A method for treating an aneurysm, said method comprising:

deploying a treatment system within the aneurysm by:

positioning at least a first double-walled filling structure across the aneurysm, the filling structure comprising a fillable space in fluid communication with an external environment surrounding the structure through a semi-permeable membrane;

filling the fillable space with a fluid filling medium so that the outer wall conforms to and contacts an inside surface of the aneurysm and an inner wall forms a first generally tubular lumen to provide a first blood flow path across the aneurysm; and maintaining apposition of the outer wall of the treatment system with the inside surface of the aneurysm after deployment through controlled fluid transfer across the semi-permeable between the fillable space and the external environment.

17. The method of claim 16, wherein filling the fillable space comprises filling the filling structure with the fluid filling medium having an osmolarity sufficient to induce an osmotic pressure differential across the membrane so as to cause transport of water molecules across the membrane until an equilibrium point is reached, wherein a water potential inside the fillable space is roughly equal to the water potential surrounding the filling structure at the equilibrium point.

18. The method of claim 16, wherein the filling structure has a volume greater than a volume of the aneurysm and the outer wall comprises folds, and maintaining apposition of the outer wall with the aneurysm comprises:

filling the structure with water through the semi-permeable membrane to further expand the filling structure thereby unfurling the folds of the outer wall to maintain apposition between the outer wall and the inside surface of the aneurysm.

19. The method of claim 16, wherein the fluid filling medium comprises a hardenable polymer, the method further comprising:

placing at least a first scaffold within at least a portion of the first generally tubular lumen and expanding the first scaffold;

supporting the tubular lumen with the first scaffold during and/or after the filling structure is being filled with the fluid filling medium; and hardening the fluid filling medium.

20. The method of claim 16, wherein maintaining apposition comprises providing a salinity within the fillable space of the filling structure that is slightly higher than a high range of blood salinities of a patient population so as to create a slightly positive osmotic pressure inside the fillable space.

21. The method of claim 16, wherein maintaining apposition comprises providing a salinity within the fillable space of the filling structure so as to provide an osmotic pressure gradient across membrane so as to avoid shrinkage of the filling structure over time.

\* \* \* \* \*